United States Patent [19]

Caswell et al.

[11] Patent Number: 4,913,828

[45] Date of Patent: Apr. 3, 1990

[54] CONDITIONING AGENTS AND COMPOSITIONS CONTAINING SAME

[75] Inventors: Debra S. Caswell; Mark H. Mao, both of Cincinnati, Ohio

[73] Assignee: The Procter & Gamble Company, Cincinnati, Ohio

[21] Appl. No.: 61,063

[22] Filed: Jun. 10, 1987

[51] Int. Cl.$^4$ .......................... C11D 9/30; C11D 9/48
[52] U.S. Cl. ...................... 252/88; 252/547; 252/DIG. 5
[58] Field of Search .................. 252/8.8, 8.75, 547, 252/DIG. 5

[56] References Cited

U.S. PATENT DOCUMENTS

| | | | |
|---|---|---|---|
| 2,691,636 | 10/1954 | Stayner et al. | 252/152 |
| 3,055,777 | 9/1962 | Grad | 117/212 |
| 3,686,025 | 8/1972 | Morton | 117/140 R |
| 3,696,056 | 10/1972 | Inamorato | 252/525 |
| 3,812,044 | 5/1974 | Connor | 252/89 |
| 3,886,075 | 5/1975 | Bernadino | 252/8.75 |
| 3,936,537 | 2/1976 | Baskerville, Jr. et al. | 427/242 |
| 3,959,155 | 5/1976 | Montgomery | 252/8.8 |
| 4,049,858 | 9/1977 | Murphy | 428/136 |
| 4,058,489 | 11/1977 | Hellsten | 252/547 |
| 4,095,946 | 6/1978 | Jones et al. | 8/137 |
| 4,126,674 | 11/1978 | Mausher | 424/31 |
| 4,173,539 | 11/1979 | Rule et al. | 252/8.8 |
| 4,272,386 | 6/1981 | Draper | 252/8.6 |
| 4,292,035 | 9/1981 | Battrell | 8/137 |
| 4,294,710 | 10/1981 | Hardy et al. | 252/8.8 |
| 4,303,543 | 12/1981 | Mansy | 252/117 |
| 4,329,390 | 2/1980 | Danner | 428/264 |
| 4,375,416 | 3/1983 | Crisp et al. | 252/8.7 |
| 4,557,853 | 12/1985 | Collins | 252/128 |
| 4,597,898 | 7/1986 | Vander Meer | 252/8.8 |
| 4,638,907 | 1/1987 | Bedenk | 206/0.5 |
| 4,661,267 | 4/1987 | Dekker | 252/529 |
| 4,786,369 | 11/1988 | Kanfer | 252/120 |

FOREIGN PATENT DOCUMENTS

| | | |
|---|---|---|
| 818419 | 7/1969 | Canada . |
| 1186458 | 5/1985 | Canada . |
| 133804 | 6/1985 | European Pat. Off. . |
| 1077103 | 7/1967 | United Kingdom . |
| 1077104 | 7/1967 | United Kingdom . |
| 1230792 | 5/1971 | United Kingdom . |
| 1514276 | 6/1978 | United Kingdom . |

Primary Examiner—John F. Niebling
Assistant Examiner—Isabelle Rodriguez
Attorney, Agent, or Firm—Leonard W. Lewis; David K. Dabbiere; Steven J. Goldstein

[57] ABSTRACT

Disclosed are alkyl amine-anionic surfactant ion-pair-/wax composites useful as fiber- and fabric-conditioning agents. Also disclosed are compositions containing these conditioning agents such as fabric detergent compositions, shampoos, hair conditioners and dryer- and washer-added fabric conditioners.

40 Claims, No Drawings

CONDITIONING AGENTS AND COMPOSITIONS CONTAINING SAME

TECHNICAL FIELD

This invention relates to fiber- and fabric-conditioning agents and more particularly to compositions containing these agents such as fabric detergent compositions, shampoos, hair conditioners and dryer- and washer-added fabric conditioning compositions.

BACKGROUND OF THE INVENTION

High electrostatic charges in various fibrous materials such as hair and clothing cause undesirable effects such as clinging or repelling of the fibers. For example, in the laundry detergent field, numerous attempts have been made to formulate laundry detergent compositions which provide the good cleaning performance expected of them and which also have good textile conditioning properties. For example, attempts have been made to incorporate cationic textile conditioners in anionic surfactant-based built detergent compositions employing various means of overcoming the natural interaction between the anionic surfactants and cationic conditioners. For instance, U.S. Pat. No. 3,936,537, Baskerville et al., issued Feb. 3, 1976, discloses detergent compositions comprising organic surfactant, builders, and, in particulate form (10 to 500 microns), a quaternary ammonium softener combined with a poorly water-soluble dispersion inhibitor which inhibits premature dispersion of the cationic in the wash liquor. Even in these compositions some compromise between cleaning and softening effectiveness has to be accepted. Another approach to provide detergent compositions with softening ability has been to employ nonionic surfactants (instead of anionic surfactants) with cationic softeners. Compositions of this type have been described in, for example, German Patent 1,220,956, assigned to Henkel, issued Apr. 4, 1964; and in U.S. Pat. No. 3,607,763, Salmen et al., issued Sept. 21, 1971. However, the detergency benefits of nonionic surfactants are inferior to those of anionic surfactants, so overall performance suffers.

Other laundry detergent compositions have employed tertiary amines along with anionic surfactants to act as textile conditioners. British Pat. No. 1,514,276, Kengon, published June 14, 1978, employs certain tertiary amines with two long chain alkyl or alkenyl groups and one short chain alkyl group. These amines are useful as fabric softeners in detergent compositions when their isoelectric point is such that they are present as a dispersion of negatively charged droplets in the normally alkaline wash liquor, and in a more cationic form at the lower pH of a rinse liquor, and so become substantive to fabrics. The use of such amines, among others, in detergent compositions has also been previously disclosed in British Pat. No. 1,286,054, assigned to Colgate-Palmolive, published Aug. 16, 1972, British Pat. No. 1,514,276, assigned to Unilever, published June 14, 1978, and in U.S. Pat. No. 4,375,416, Crisp et al., issued Mar. 1, 1983.

Another approach to provide anionic detergent compositions with textile softening ability has been the use of smectite-type clays, as described in U.S. Pat. No. 4,062,647, Storm et al., issued Dec. 13, 1977. These compositions, although they clean well, require large contents of clay for effective softening. The use of clay together with a water-insoluble cationic compound and an electrically conductive metal salt as a softening composition adapted for use with anionic, nonionic, zwitterionic and amphoteric surfactants has been described in British Pat. No. 1,483,627, assigned to Procter & Gamble, published Aug. 24, 1977.

British Patent Applications 1,077,103 and 1,077,104, assigned to Bayer, published July 26, 1967, disclose amine-anionic surfactant ion-pair complexes useful as antistatic agents. These complexes are applied directly to the fabric from an aqueous carrier. Fatty acid-amine ion-pair complexes in granular detergents are disclosed in European Patent Application 133,804, Burckett-St. Laurent et al., published June 3, 1985.

Other methods of conditioning fabrics include adding fabric conditioners during the rinse cycle of the washing process and also adding a conditioner during the drying process. See, for example, U.S. Pat. No. 4,233,164, Davis, issued Nov. 11, 1980.

While shampoos which contain conditioning aids have been disclosed, they have not been totally satisfactory for a variety of reasons. As with laundry detergent-/softener combinations, there are compatibility problems between good cleaning anionic surfactants and the hair conditioning agents which are generally cationic. To alleviate this undesirable interaction, other surfactants, such as nonionics, amphoterics and zwitterionics, were examined by workers in the field. These efforts are reflected in patents issued in the conditioning shampoo area. See, for example, U.S. Pat. No. 3,849,348, issued Nov. 19, 1974 to Hewitt and U.S. Pat. No. 3,822,312, issued July 2, 1974 to Sato.

The use of these non-anionic surfactants solved many of the compatibility problems but still did not provide complete answers in all areas. For instance, none of these approaches effectively solved the problem of "fly-away" hair caused by electrostatic charge. It clearly would be highly desirable to be able to formulate a shampoo which provides both effective cleaning and hair conditioning benefits.

Surprisingly, it has been found that certain ion-pair wax composites are excellent conditioning agents when applied alone, or when used with various carriers such as washer-added and dryer-added sheets, shampoos or laundry detergents. Additionally, these composites are stable when used in detergent compositions, even those containing very aggressive surfactants such as the alkyl sulfates and alkyl ethoxylated sulfates.

It is therefore an object of the present invention to provide ion-pair wax composites with superior conditioning properties.

A further object of the present invention is to provide compositions, such as shampoos, laundry detergents and washer-added and dryer-added fabric conditioners with excellent conditioning properties.

A further object of the present invention is to provide conditioning agents which can be used in laundry detergents containing very aggressive detergent surfactants such as the alkyl sulfates and the alkyl ethoxylated sulfates.

SUMMARY OF THE INVENTION

The present invention relates to conditioning agents comprising:
(i) from about 1% to about 99% of an alkyl amine-anionic surfactant ion-pair complex having the formula:

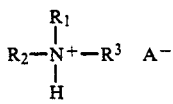

wherein $R_1$ and $R_2$ can independently be $C_{16}$ to $C_{20}$ alkyl or alkenyl and $R^3$ is H or $CH_3$, and A is an anionic surfactant selected from the group consisting of alkyl sulfonates, aryl sulfonates, alkylaryl sulfonates, alkyl sulfates, alkyl ethoxylated sulfates, dialkyl sulfosuccinates, ethoxylated alkyl sulfonates, alkyl oxybenzene sulfonates, acyl isethionates, acyl alkyl taurates olefin sulfonates and paraffin sulfonates, and mixtures of such ion-pair complexes; and, (ii) from about 1% to about 99% of a nonsilicone wax.

These conditioning agents can be delivered from a variety of substrates such as laundry detergents, shampoos, washer-added and dryer-added conditioners, and the like.

DETAILED DESCRIPTION OF THE INVENTION

The components of the present invention are described in detail below. As used herein, the percentages are all by weight unless otherwise stated.

Conditioning Agent

Starting alkylamines are of the formula:

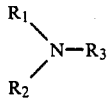

wherein $R_1$ and $R_2$ are independently $C_{16}$ to $C_{20}$ alkyl or alkenyl, preferably $C_{16}$ to $C_{18}$ alkyl or alkenyl, and most preferably $C_{16}$ to $C_{18}$ alkyl and $R_3$ is H or $CH_3$, preferably H. Suitable non-limiting examples of starting amines include hydrogenated ditallow amine, hydrogenated ditallow methyl amine, unhydrogenated ditallow amine, unhydrogenated ditallow methyl amine, dipalmityl amine, dipalmityl methyl amine, distearyl amine, distearyl methyl amine, diarachidyl amine, diarachidyl methyl amine, palmityl stearyl amine, palmityl stearyl methyl amine, palmityl arachidyl amine, palmityl arachidyl methyl amine, stearyl arachidyl amine, and stearyl arachidyl methyl amine. Most preferred is hydrogenated ditallow amine.

The anionic surfactants (A) useful in the ion-pair complex portion of the composites of the present invention are the $C_1$ to $C_{20}$ alkyl sulfonates, aryl sulfonates, $C_1$ to $C_{20}$ alkylaryl sulfonates, $C_1$ to $C_{20}$ alkyl sulfates, $C_1$ to $C_{20}$ alkyl ethoxylated sulfates, dialkyl sulfosuccinates, ethoxylated alkyl sulfonates, alkyl oxybenzene sulfonates, acyl isethionates, acylalkyl taurates, olefin sulfonates and $C_{12}$ to $C_{18}$ paraffin sulfonates. As used herein, the term linear alkylbenzene sulfonate refers to a linear alkyl chain to which a benzene sulfonate is attached wherein said benzene sulfonate can be positioned at any carbon atom of said chain, primarily at the second carbon for those alkyl chains containing three or more carbon atoms. Preferred anionic surfactants (A) are $C_1$ to $C_{20}$ alkyl sulfonates, $C_1$ to $C_{20}$ alkylaryl sulfonates, $C_{12}$ to $C_{18}$ paraffin sulfonates and aryl sulfonates. More preferred are the aryl sulfonates and the $C_1$-$C_{20}$ alkylaryl sulfonates. Even more preferred are $C_1$-$C_{13}$ linear alkylbenzene sulfonates and benzene sulfonates. Even more preferred are $C_2$-$C_8$ linear alkylbenzene sulfonates. Most preferred is cumene sulfonate ($C_3$LAS). These classes of anionic surfactants are more fully described below.

Non-limiting examples of ion-pair complexes suitable for use in the composites of the present invention include:

ditallow amine (hydrogenated or unhydrogenated) complexed with a linear $C_1$-$C_{20}$ alkylbenzene sulfonate (LAS), ditallow methyl amine (hydrogenated or unhydrogenated) complexed with a $C_1$-$C_{20}$ LAS, dipalmityl amine complexed with a $C_1$-$C_{20}$ LAS, dipalmityl methyl amine complexed with a $C_1$-$C_{20}$ LAS, distearyl amine complexed with a $C_1$-$C_{20}$ LAS, distearyl methyl amine complexed with a $C_1$-$C_{20}$ LAS, diarachidyl amine complexed with a $C_1$-$C_{20}$ LAS, diarachidyl methyl amine complexed with a $C_1$-$C_{20}$ LAS, palmityl stearyl amine complexed with a $C_1$-$C_{20}$ LAS, palmityl stearyl methyl amine complexed with a $C_1$-$C_{20}$ LAS, palmityl arachidyl amine complexed with a $C_1$-$C_{20}$ LAS, palmityl arachidyl methyl amine complexed with a $C_1$-$C_{20}$ LAS, stearyl arachidyl amine complexed with a $C_1$-$C_{20}$ LAS, stearyl arachidyl methyl amine complexed with a $C_1$-$C_{20}$ LAS, ditallow amine (hydrogenated or unhydrogenated) complexed with a $C_1$-$C_{20}$ alkyl sulfonate (AS), ditallow methyl amine (hydrogenated or unhydrogenated) complexed with a $C_1$-$C_{20}$ AS, dipalmityl amine complexed with a $C_1$-$C_{20}$ AS, dipalmityl methyl amine complexed with a $C_1$-$C_{20}$ AS, distearyl amine complexed with a $C_1$-$C_{20}$ AS, distearyl methyl amine complexed with a $C_1$-$C_{20}$ AS, diarachidyl amine complexed with a $C_1$-$C_{20}$ AS, diarachidyl methyl amine complexed with a $C_1$-$C_{20}$ AS, palmityl stearyl amine complexed with a $C_1$-$C_{20}$ AS, palmityl stearyl methyl amine complexed with a $C_1$-$C_{20}$ AS, palmityl arachidyl amine complexed with a $C_1$-$C_{20}$ AS, palmityl arachidyl methyl amine complexed with a $C_1$-$C_{20}$ AS, stearyl arachidyl amine complexed with a $C_1$-$C_{20}$ AS, stearyl arachidyl methyl amine complexed with a $C_1$-$C_{20}$ AS, ditallow amine (hydrogenated or unhydrogenated) complexed with an aryl sulfonate, ditallow methyl amine (hydrogenated or unhydrogenated) complexed with an aryl sulfonate, dipalmityl amine complexed with an aryl sulfonate, dipalmityl methyl amine complexed with an aryl sulfonate, distearyl amine complexed with an aryl sulfonate, distearyl methyl amine complexed with an aryl sulfonate, diarachidyl amine complexed with an aryl sulfonate, diarachidyl methyl amine complexed with an aryl sulfonate, palmityl stearyl amine complexed with an aryl sulfonate, palmityl stearyl methyl amine complexed with an aryl sulfonate,
palmityl arachidyl amine complexed with an aryl sulfonate, and
palmityl arachidyl methyl amine complexed with an aryl sulfonate,
stearyl arachidyl amine complexed with an aryl sulfonate, and
stearyl arachidyl methyl amine complexed with an aryl sulfonate,
and mixtures of these ion-pair complexes.

More preferred are complexes formed from the combination of ditallow amine (hydrogenated or unhydrogenated) complexed with an aryl sulfonate or $C_1$-$C_{20}$ alkylaryl sulfonate and ditallow methyl amine (hydrogenated or unhydrogenated) complexed with an aryl sulfonate or with a $C_1$-$C_{20}$ alkylaryl sulfonate. Even more preferred are those complexes formed from hydrogenated ditallow amine complexed with a benzene sulfonate or a $C_1$-$C_{13}$ linear alkylbenzene sulfonate. Even more preferred are complexes formed from hydrogenated ditallow amine complexed with a $C_2$-$C_8$ linear alkylbenzene sulfonate. Most preferred are complexes formed from hydrogenated ditallow amine and cumene sulfonate.

In order to form the ion-pair complex, the amine and surfactant components are combined in a molar ratio of alkylamine to surfactant ranging from about 1:10 to about 10:1, preferably from about 1:1 to about 3:1. This can be accomplished by any of a variety of means, including but not limited to, adding the anionic surfactant (in acid form) to a molten amine (50° C.-150° C.) while applying vigorous agitation, and allowing the molten complex to cool while continuing the mechanical stirring.

Other methods of forming the ion-pair complex include dissolving the components in an organic solvent, or heating the amine to a liquid state and then adding this molten amine component to a heated acidified aqueous solution of the anionic surfactant, and extracting the ion-pair complex by using a solvent, such as chloroform.

The complexing of the amine and the anionic surfactant results in an entity (ion-pair) which is chemically distinct from either of the two starting materials.

The complexes are further characterized by their melting points, which generally lie in the range of from about 10° C. to about 90° C. A particularly preferred complex, which is comprised of a hydrogenated ditallow amine complexed with cumene sulfonate surfactant (from acid or salt form) in a 1:1 molar ratio, has a melting point of about 40° C.

Nonsilicone waxes

The waxes suitable for use in the present invention are nonsilicone waxes including but not limited to: animal waxes, such as beeswax, lanolin, spermaceti and whale oil; vegetable waxes, such as carnuba, candellila, sugar cane, and jojoba; fossil mineral waxes, such as montan, ozokerite and Utah wax; hydrocarbon waxes, such as mineral oil, petrolatum, paraffin and microcrystalline; synthetic waxes, such as polyethylene (polythene), sterone, gersthofen, acrowax, opelwax, cardis, and carbowax.

These classes of waxes are fully described in "The Chemistry and Technology of Waxes", A. H. Warth, 2nd Edition, reprinted in 1960, Reinhold Publishing Corporation, pp 391-393 and 421; "The Petroleum Chemicals Industry", R. F. Goldstein and A. L. Waddeam, 3rd Edition (1967), E and F. N. Span Ltd, pp 33-40; "The Chemistry and Manufacture of Cosmetics", M. G. DeNavarre, 2nd edition (1970), Van Nostrand & Company, pp 354-376; and in "Encyclopedia of Chemical Technology", Vol. 24, Kirk-Othmer, 3rd Edition (1979) pp 466-481, all of which are incorporated herein by reference.

Preferred for use in the present invention are the hydrocarbon waxes known as paraffin and microcrystalline waxes, as well as mixtures of these waxes. The terms "paraffin wax" and "microcrystalline wax" are well known in the art and cover a somewhat variable class of substances.

1. Paraffin Waxes

Paraffin wax is macrocrystalline, brittle, and is composed of from about 40% to about 90% paraffins and the remainder is $C_{18}$ to $C_{36}$ isoalkenes and cycloalkanes. Paraffin wax is derived from crude petroleum.

When a suitable crude is obtained, it is separated into several fractions in the following sequence: gasoline, naphtha, kerosene, gas oil or fuel oil, wax distillate (also called pressable wax distillate) and cylinder stock. The wax distillate (which may be diluted with a solvent, such as kerosene, to aid in pressing and to help large crystal formation) is chilled to about −9° C. and filtered under pressure. The filter cake contains the crude paraffin wax. This is remelted and put through a process of "sweating" to remove the 20% oil present. This wax is further refined by deodorizing and bleaching before being sold as fully refined paraffin wax.

Pure paraffin wax occurs in large plate-like hexagonal crystals which differentiates it from ozokerite and the so-called microcrystalline waxes. Paraffin crystals in needle form result from the presence of impurities. In its commercial form it contains less than 1% oil.

Preferred paraffin waxes are characterized by a melting point of 120° F.-175° F. (50°-80° C.) and a penetration of 10-20 at 70° F. (25° C.) (as defined by ASTM D-1321) and a ratio of n-paraffins to iso-paraffins of from about 1:1 to about 20:1.

Particularly preferred paraffin waxes include the following which are available from Boler Petroleum Company (Wayne, Pa.):

| | MELTING POINT | n-PARAFFINS (%) | iso PARAFFINS (%) |
|---|---|---|---|
| Boler 1014 | 161-165° F. (AMP)[1] (72-74° C.) | 58 | 42 |
| Boler 1554 | 158° F. (T)[2] (70° C.) | 78 | 22 |
| Boler 1070 | 130-132° F. (AMP) (54-55° C.) | 88 | 12 |
| Boler 1072 | 126-129° F. (AMP) (52-54° C.) | 93 | 7 |
| Boler 1977 | 143° F. (T) (62° C.) | 80 | 20 |

[1]American Melting Point
[2]Melting point as determined by ASTM D-87

2. Microcrystalline Waxes

Microcrystalline waxes are relatively high melting point waxes and are distinguished from paraffin waxes by their smaller more flexible crystals and higher molecular weight. Generally they have a molecular weight in the range from about 400 to 1000. They are substantially water-insoluble but are able to be dispersed in aqueous micellar solutions of organic surfactants and/or in neat liquid organic surfactants, e.g., as colloidal or micellar solutions or as true solutions or emulsions.

As the name implies, the individual crystals of microcrystalline wax are much smaller than those of paraffin wax. In general, microcrystalline waxes are tough rather than brittle; some of them are flexible even at low temperatures. Although microcrystalline wax is largely paraffinic in its chemical nature, the compounds of which it consists are not the same as those which constitute paraffin wax. The compounds which constitute microcrystalline wax have a materially higher molecular weight and higher proportion of branched chain hydrocarbons than do those found in paraffin waxes. Microcrystalline wax is derived from oils heavier than those from which paraffin waxes are made and usually is recovered from residual oils, that is, from oils taken off as distillation bottoms. Two broad classes of microcrystalline waxes are produced: "plastic" grades, those with a penetration greater than 11 which are usually produced from crude petrolatum, and "hard" grades, which have a penetration of 11 or less, and usually are made from crude-oil tank bottoms.

Particularly preferred microcrystalline waxes are characterized by a melting point of from about 150° F. to about 220° F. (about 66° C. to about 104° C.) and a penetration of from about 0.1 to about 10 at 77° F. (25° C.). Particularly preferred are the "hard" microcrystalline petrolatum waxes known as Be Square 195, Petrolite C-1035 and Petrolite C-700 all of which are sold by the Bareco Division, Petrolite Corporation, Tulsa, Okla.

Other very effective waxes include the "hard" microcrystallines Starwax 100, Be Square 185, Mekon Whiter, and Fortrex and the "plastic" microcrystallines Ultraflex, Victory and Be Square 175, all of which are also sold by the Bareco Division.

The table below summarizes the physical properties of typical paraffin and microcrystalline waxes useful in the present invention.

| Property | Paraffin | Microcrystalline |
| --- | --- | --- |
| flash point | 204° C. | 260° C. |
| viscosity at 98.9° C., (Saybolt Units) | 40-50 | 60-120 |
| melting range | 120-175° F. (50-80° C.) | 150-220° F. (66-104° C.) |
| refractive index at 98.9° C. | 1.430-1.433 | 1.435-1.445 |
| average molecular weight | 350-420 | 400-800 |
| carbon atoms per molecule | 20-36 | 30-75 |
| other physical aspects | friable to crystalline | ductile-plastic to tough-brittle |

Mixtures of paraffin and microcrystalline waxes are particularly preferred.

The ion-pair complex and wax are combined by comelting the two components in a weight ratio of ion-pair complex to wax of from about 1:10 to about 10:1.

The criteria for selecting the composition of the ion-pair/wax composite (choice of ion pair:wax ratio, wax identity and wax:wax ratio for blends of microcrystalline and paraffin waxes) in detergent compositions are dependent on numerous factors including the physical and chemical nature of the detergent base, processing limitations, laundering conditions at the time of required active deposition, and mechanism of active distribution across fibers (e.g., machine dry vs. line dry). It is desirable to maintain as hard a particle as possible during the wash to eliminate softening of the wax (and resultant clumping) and thereby enhance dispersion and deposition of the composite. This is best accomplished by increasing the amount and/or penetration factor of the wax.

In liquid detergency compositions, such as shampoos or laundry detergents, where the composite is in intimate contact with very aggressive surfactants, such as alkyl sulfates (AS) and alkyl ethoxylated sulfates (AES), which can cause the ion-pair portion of the composite to disassociate, it is preferred that more integral ion-pair wax composites be used.

Generally, longer chain ($C_6$-$C_{13}$) LAS ion-pairs have melting points in the range of 15°-25° C. and are gelatinous (soft). Shorter chain ($C_1$-$C_5$ and benzene sulfonate) LAS ion-pairs have melting points in the range of 35°-80° C. and are more crystalline (hard). Preferred paraffin waxes have melting points in the 120°-175° F. (50°-80° C.) range with penetration values of about 10-20 at 77° F. (25° C.). Preferred microcrystalline waxes are categorized as "plastic" (m.p. 150°-185° F. (66°-85° C.), pen/77° F. (25° C.) 25-35) or "hard" (m.p. 185°-210° F. (85°-104° C.), pen/77° F. (25° C.) 3-8). Paraffin waxes are made of large well-formed crystals and contain considerably more n-paraffins than do microcrystalline waxes. However, as little as 1% microcrystalline wax added to paraffin can significantly alter the morphology of the blend resulting in small ("micro") crystals. If more microcrystalline wax is added, the penetration of the blend can be altered. Therefore, one can achieve unlimited variability in the resultant ion-pair/wax composite using mixtures of paraffin and microcrystalline waxes.

In the liquid detergency context, in order to obtain ion-pair/wax composites which are integral, soft ion-pairs (IP's) are preferably used along with harder (penetration of less than 10) wax blends and, except in very mild detergent bases (e.g., those not containing AS and AES), require nearly an equal weight of wax to form an optimized protection network (e.g., $C_8$IP:paraffin:microcrystalline ratio of 50:30:20). Hard IP's are preferably used along with moderately soft wax blends (penetration of about 10-20) for protection and can be used in higher IP:wax ratios even in aggressive (AES-containing) detergent bases (e.g., $C_3$IP:paraffin ratio of 75:25). Hard IP's can be prilled with most any wax. Soft IP's can be made "prillable" by introducing large quantities of hard microcrystalline wax into the composite.

Any composite can be made, for example, by comelting the components, cryogenically freezing the comelt with liquid nitrogen, grinding and sieving the frozen composite. While cold, the resulting particles can be incorporated into a liquid detergent by shaking or mechanically stirring and they remain well dispersed. However, only hard particles should be formulated into a granular detergent, since sticky particles will cause clumping and inadequate dispersion in the wash.

Harder composites can be prilled in the usual manner (i.e., forcing the well-circulated comelt through a heated nozzle into cooled atmospheric temperatures) and easily dispersed into liquid detergents or granular detergents.

In contrast to liquid detergents, the lack of intimate contact between the ion-pair/wax composite and base components in a granular detergent allows for greater flexibility (e.g., in terms of wax identity and IP:wax ratios) when formulating such granular compositions.

Mild (non-AS/AES containing) detergent bases can contain almost any IP/wax combination in IP:wax ratios as high as 80:20. However, for more aggressive (AS- and AES-containing) matrices it is more difficult to maintain particle integrity in the composition; therefore, the combinations listed above are preferred.

It has been found that in order for these static control agents to impart their benefits when delivered from a detergency matrix such as a shampoo or laundry detergent, they preferably have an average particle diameter of from about 10 to about 300 microns, more preferably from about 10 to about 250 microns, more preferably from about 10 to about 200 microns, and most preferably from about 10 microns to about 150 microns. For aqueous dispersions, such as rinse-added fabric softeners, they preferably have an average particle diameter of from about 1 nanometer to about 1000 nanometers, more preferably from about 20 to about 500 nanometers. In such applications, these waxes should not be solubilized. These particle sizes are not required for delivery from substrates such as sprays and dryer-added and washer-added fabric softeners from a sheet as described herein. The term "average particle diameter" represents the mean particle size diameter of the actual particles of a given material. The mean is calculated on a weight percent basis. The mean is determined by conventional analytical techniques such as, for example, laser light diffraction or microscopic determination utilizing a light or SEM. For detergency compositions, preferably greater than 50% by weight, more preferably greater than 70% by weight, and most preferably greater than 95% by weight, of the particles have actual diameters which fall within the range of from about 10 to about 300 microns, preferably from about 10 to about 250 microns, more preferably from about 10 to about 200 microns, and most preferably from about 10 microns to about 150 microns. When less than 5% of the particles have an average diameter of above 150 microns, problems with laundry appliance compatibility can be avoided. For aqueous dispersions such as rinse-added fabric softeners, preferably greater than 50% by weight, more preferably greater than 70% by weight, and most preferably greater than 95% by weight of the particles have an average particle diameter of from about 1 to about 1000 nanometers, preferably from about 20 to about 500 nanometers. These sub-micron size particles are achieved by adding a hot melt of the composite to the base and using high shear to disperse the particles.

The particle sizes can be achieved by, for example, mechanically grinding the resulting ion-pair/wax composite in blenders (e.g., an Oster ® blender) or in large scale mills (e.g., a Wiley ® Mill) and then sieving the ground material to the desired particle size range.

Composites which are gelatinous or soft at room temperature can be mechanically ground to achieve the desired particle size after flash freezing by using, for example, liquid nitrogen.

The shorter LAS chain length ion-pair complexes ($C_1$-$C_5$ and benzene sulfonate) allow for prilling of the ion-pair/wax composite due to their higher melting points. However, higher levels of wax and/or the use of harder waxes (penetration of less than 10) will also allow for prilling of the longer chain length ion-pairs ($C_6$-$C_{13}$). The comelted ion-pair and wax is kept well mixed by recirculation to avoid separation of the components. The hot melt is hydraulically forced through a heated nozzle (or atomized with air injection) into ambient or cryogenically cooled atmospheric temperatures resulting in spherical particles with an average particle diameter of 10-150 microns. These particles are then collected and applied to the desired carrier to deliver the aforedescribed benefits. Ion-pair/wax composites which allow for prilling are preferred for use in granular and liquid detergents. Highly preferred are nonagglomerated spheres with an average particle diameter of about 10 to about 150 microns with less than 5% (by weight) of the particles having a diameter of greater than about 150 microns.

COMPOSITIONS

When used in a carrier, the ion-pair/wax composite is prepared separately from the balance of the composition, and is preferably then added in such a way as to insure that the composites are homogeneously dispersed therein or applied thereon.

The conditioning agents of the present invention are especially useful for imparting conditioning from a variety of carriers. Suitable carriers for use of these agents include detergent compositions (both granular and liquid), shampoo compositions, and washer-added and dryer-added fabric conditioners which will be more fully described below.

DETERGENT COMPONENTS

It has been found that the conditioning agents of the present invention, unlike those of the prior art, can be incorporated into the granular and liquid detergent compositions of the present invention with little, if any, detrimental effect on cleaning.

Laundry detergent compositions of the present invention provide fabric care benefits across a variety of laundry conditions, that is, machine or hand washing and machine drying and also machine or hand washing and line drying. Additionally, these same conditioning agents can be used with a variety of surfactant systems.

The composites are typically used herein at levels of about 0.1% to about 20.0%, most preferably 0.5 to 15.0% of the detergent composition.

Detergent Surfactant

The amount of detergent surfactant included in the compositions of the present invention can vary from about 1% to about 98% by weight of the composition, depending upon the particular surfactant(s) used and the effects desired. Preferably, the detergent surfactant(s) comprises from about 10% to about 60% by weight of the composition. Combinations of anionic, preferably alkyl sulfates, alkyl ethoxylated sulfates, linear alkyl benzene sulfonates, and nonionic, preferably alkyl polyethoxylated alcohols surfactants are preferred for optimum combined cleaning and textile softening performance, but other classes of surfactants such as semi-polar, ampholytic, zwitterionic, or cationic may be used. Mixtures of all of these surfactants can also be used. As is recognized in the art, granular detergents incorporate the salt forms of the following surfactants while liquids incorporate the acid form, where stable.

A. Anionic Surfactants

Anionic surfactants suitable for use in the present invention are the sulfates and sulfonates and are generally disclosed in U.S. Pat. No. 3,929,678, Laughlin et al., issued Dec. 30, 1975, at column 23, line 58 through column 29, line 23 and in U.S. Pat. No. 4,294,710, Hardy et al., issued Oct. 13, 1981, both of which are incorporated herein by reference. Classes of useful anionic surfactants include:

1. Ordinary alkali metal soaps, such as the sodium, potassium, ammonium and alkylolammonium salts of higher fatty acids containing from about 8 to about 24 carbon atoms, preferably from about 10 to about 20 carbon atoms. Preferred alkali metal soaps are sodium laurate, sodium stearate, sodium oleate and potassium palmitate.

2. Water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.)

Examples of this group of anionic surfactants are the sodium and potassium alkylbenzene sulfonates in which the alkyl group contains from about 9 to about 15 carbon atoms, in straight chain or branched chain configuration, e.g., those of the type described in U.S. Pat. No. 2,220,099, Guenther et al., issued Nov. 5, 1940, and U.S. Pat. No. 2,477,383, Lewis, issued Dec. 26, 1946. Especially useful are linear straight chain alkylbenzene sulfonates in which the average number of carbon atoms in the alkyl group is from about 11 to about 13, abbreviated as $C_{11}$–$C_{13}$LAS.

Other anionic surfactants of this type include sodium alkyl glyceryl ether sulfonates, especially those ethers of higher alcohols derived from tallow and coconut oil; sodium coconut oil fatty acid monoglyceride sulfonates and sulfates and sodium or potassium salts of alkyl phenol ethylene oxide ether sulfates containing from about 1 to about 10 units of ethylene oxide per molecule and wherein the alkyl groups contain from about 8 to about 12 carbon atoms.

Also included are water-soluble salts of esters of alpha-sulfonated fatty acids containing from about 6 to about 20 carbon atoms in the fatty acid group and from about 1 to about 10 carbon atoms in the ester group; water-soluble salts of 2-acyloxyalkane-1-sulfonic acids containing from about 2 to about 9 carbon atoms in the acyl group and from about 9 to about 23 carbon atoms in the alkane moiety; water-soluble salts of olefin sulfonates containing from about 12 to about 24 carbon atoms; and beta-alkyloxy alkane sulfonates containing from about 1 to about 3 carbon atoms in the alkyl group and from about 8 to about 20 carbon atoms in the alkane moiety.

The present compositions may also contain an alcohol ethoxylate sulfate surfactant of the formula RO($C_2$—$H_4O$)$_m$$SO_3$M, wherein R is a $C_{10}$–$C_{16}$ alkyl (preferred) or hydroxyalkyl group, m is from about 0.5 to about 4, and M is a compatible cation. This class of surfactants is described in U.S. Pat. No. 4,807,219, to Hughes, issued Mar. 26, 1985, which is incorporated herein by reference. This surfactant represents from about 8% to about 18%, preferably from about 9% to about 14%, by weight (on an acid basis) of the composition.

Preferred alcohol ethoxylate sulfate surfactants of the above formula are those wherein the R substituent is a $C_{12}$–$C_{15}$ alkyl group and m is from about 1.5 to about 3. Examples of such materials are $C_{12}$–$C_{15}$ alkyl polyethoxylate (2.25) sulfate ($C_{12-15}E_{2.25}S$); $C_{14-15}E_{2.25}S$; $C_{12-13}E_{1.5}S$; $C_{14-15}E_3S$; and mixtures thereof.

3. Anionic phosphate surfactants.
4. N-alkyl substituted succinamates.

B. Nonionic Surfactants

Suitable nonionic surfactants are generally disclosed in U.S. Pat. No. 3,929,678, Laughlin et al., issued Dec. 30, 1975, at column 13, line 14 through column 16, line 6, incorporated herein by reference. Classes of useful nonionic surfactants include:

1. The polyethylene oxide condensates of alkyl phenols. These compounds include the condensation products of alkyl phenols having an alkyl group containing from about 6 to about 12 carbon atoms in either a straight chain or branched chain configuration with ethylene oxide, the ethylene oxide being present in an amount equal to from about 5 to about 25 moles of ethylene oxide per mole of alkyl phenol. Examples of compounds of this type include nonyl phenol condensed with about 9.5 moles of ethylene oxide per mole of phenol; dodecyl phenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available non-ionic surfactants of this type include Igepal C-630, marketed by the GAF Corporation; and Triton X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 4 to about 10 moles of ethylene oxide per mole of alcohol. Examples of such ethoxylated alcohols include the condensation product of myristyl alcohol with about 10 moles of ethylene oxide per mole of alcohol; and the condensation product of coconut alcohol (a mixture of fatty alcohols with alkyl chains varying in length from 10 to 14 carbon atoms) with about 9 moles of ethylene oxide. Examples of commercially available nonionic surfactants of this type include Tergitol 15-S-9 (the condensation product of $C_{11}$–$C_{15}$ linear alcohol with 9 moles ethylene oxide), Tergitol 24-L-6 NMW (the condensation product of $C_{12}$–$C_{14}$ primary alcohol with 6 moles ethylene oxide with a narrow molecular weight distribution), both marketed by Union Carbide Corporation; Neodol 45-9 (the condensation product of $C_{14}$–$C_{15}$ linear alcohol with 9 moles of ethylene oxide), Neodol 23-6.5 (the condensation product of $C_{12}$–$C_{13}$ linear alcohol with 6.5 moles of ethylene oxide), Neodol 45-7 (the condensation product of $C_{14}$–$C_{15}$ linear alcohol with 7 moles of ethylene oxide), Neodol 45-4 (the condensation product of $C_{14}$–$C_{15}$ linear alcohol with 4 moles of ethylene oxide), marketed by Shell Chemical Company, and Kyro EOB (the condensation product of $C_{13}$–$C_{15}$ alcohol with 9 moles ethylene oxide), marketed by The Procter & Gamble Company.

3. The condensation products of ethylene oxide with a hydrophobic base formed by the condensation of propylene oxide with propylene glycol. The hydrophobic portion of these compounds has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic surfactants, marketed by Wyandotte Chemical Corporation.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds, marketed by Wyandotte Chemical Corporation.

5. Semi-polar nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Preferred semi-polar nonionic detergent surfactants are the amine oxide surfactants having the formula

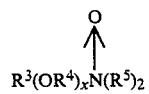

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

Preferred amine oxide surfactants are $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.5 to about 10, preferably from about 1.5 to about 3, most preferably from about 1.6 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

The preferred alkylpolyglycosides have the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

7. Fatty acid amide surfactants having the formula:

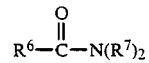

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C_2H_4O)_xH$ where x varies from about 1 to about 3.

Preferred amides are $C_8$–$C_{20}$ ammonia amides, monoethanolamides, diethanolamides, and isopropanolamides.

C. Ampholytic Surfactants

Ampholytic surfactants can be broadly described as aliphatic derivatives of secondary or tertiary amines, or aliphatic derivatives of heterocyclic secondary and tertiary amines in which the aliphatic radical can be straight or branched chain and wherein one of the aliphatic substituents contains from about 8 to about 18 carbon atoms and at least one of the aliphatic substituents contains an anionic water-solubilizing group, e.g., carboxy, sulfonate, sulfate. See U.S. Pat. No. 3,929,678, Laughlin et al., issued Dec. 30, 1975, column 19, line 38 through column 22, line 48, incorporated herein by reference, for examples of ampholytic surfactants useful herein.

D. Zwitterionic Surfactants

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678, Laughlin et al., issued Dec. 30, 1975, column 19, line 38 through column 22, line 48, incorporated herein by reference, for examples of zwitterionic surfactants useful herein.

E. Cationic Surfactants

Cationic surfactants are the least preferred detergent surfactants useful in detergent compositions of the present invention. Cationic surfactants comprise a wide variety of compounds characterized by one or more organic hydrophobic groups in the cation and generally by a quaternary nitrogen associated with an acid radical. Pentavalent nitrogen ring compounds are also considered quaternary nitrogen compounds. Suitable anions are halides, methyl sulfate and hydroxide. Tertiary amines can have characteristics similar to cationic surfactants at washing solutions pH values less than about 8.5.

Suitable cationic surfactants include the quaternary ammonium surfactants having the formula:

$$[R^2(OR^3)_y][R^4(OR^3)_y]_2R^5N^+X^-$$

wherein $R^2$ is an alkyl or alkyl benzyl group having from about 8 to about 18 carbon atoms in the alkyl chain; each $R^3$ is independently selected from the group consisting of $-CH_2CH_2-$, $-CH_2CH(CH_3)-$, $-CH_2CH(CH_2OH)-$, and $-CH_2CH_2CH_2-$; each $R^4$ is independently selected from the group consisting of $C_1$–$C_4$ alkyl, $C_1$–$C_4$ hydroxyalkyl, benzyl, ring structures formed by joining the two $R^4$ groups, $-CH_2$CHOHCHOHCHOR$^6$CHOHCH$_2$OH wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Preferred examples of the above compounds are the alkyl quaternary ammonium surfactants, especially the mono-long chain alkyl surfactants described in the above formula when $R^5$ is selected from the same groups as $R^4$. The most preferred quaternary ammonium surfactants are the chloride, bromide and methylsulfate $C_8$–$C_{16}$ alkyl trimethylammonium salts, $C_8$–$C_{16}$ alkyl di(hydroxyethyl)methylammonium salts, the $C_8$–$C_{16}$ alkyl hydroxyethyldimethylammonium salts, and $C_8$–$C_{16}$ alkyloxypropyltrimethylammonium salts. Of the above, decyl trimethylammonium methylsulfate, lauryl trimethylammonium chloride, myristyl trimethylammonium bromide and coconut trimethylammonium chloride and methylsulfate are particularly preferred.

A more complete disclosure of these and other cationic surfactants useful herein can be found in U.S. Pat. No. 4,228,044, Cambre, issued Oct. 14, 1980, incorporated herein by reference.

Detergent Builders

Detergent compositions of the present invention contain inorganic and/or organic detergent builders to assist in mineral hardness control. These builders comprise from 0% to about 80% by weight of the compositions. Built liquid formulations preferably comprise from about 5% to about 50%, preferably about 5% to about 30%, by weight of detergent builder.

Useful builders include the various alkali metal, ammonium and substituted ammonium polyacetates, inorganic phosphates, polyphosphates, phosphonates, polyphosphonic acids, silicates, carbonates, alumino silicates, alkali metal silicates, alkali metal carbonates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, nitrilotriacetic acid, oxydisuccinic acid, mellitic acid, benzene polycarboxylic acids, and citrate. The citrate (preferably in the form of an alkali metal or alkanolammonium salt) is generally added to the composition as citric acid, but can be added in the form of a fully neutralized salt.

Highly preferred polycarboxylate builders are disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other builders include the carboxylated carbohydrates disclosed in U.S. Pat. No. 3,723,322, Diehl, issued Mar. 28, 1973, incorporated herein by reference.

A class of useful phosphorus-free detergent builder materials have been found to be ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et al, U.S. Pat. No. 3,635,830, issued Jan. 18, 1972, both of which are incorporated herein by reference.

A specific type of ether polycarboxylates useful as builders in the present invention are those having the general formula:

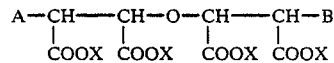

wherein A is H or OH; B is H or

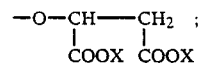

and X is H or a salt-forming cation. For example, if in the above general formula A and B are both H, then the compound is oxy-dissuccinic acid and its water-soluble salts. If A is OH and B is H, then the compound is tartrate monosuccinic acid (TMS) and its water-soluble salts. If A is H and B is

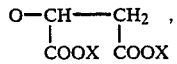

then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

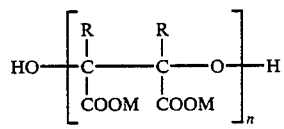

wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen).

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Other useful builders include the $C_5$–$C_{20}$ alkyl succinic acids and salts thereof.

Useful builders also include sodium and potassium carboxymethyloxymalonate, carboxymethyloxysuccinate, cis-cyclohexanehexacarboxylate, cis-cyclopentanetetracarboxylate phloroglucinol trisulfonate, water-soluble polyacrylates (having molecular weights of from about 2,000 to about 200,000, for example), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

The succinate builders are preferably used in the form of their water-soluble salts, including the sodium, potassium, ammonium and alkanolammonium salts.

Specific examples of succinate builders include: lauryl succinate, myristyl succinate, palmityl succinate, 2-dodecenyl succinate (preferred), 2-pentadecenyl succinate, and the like.

Other useful detergency builders include the $C_{10}$–$C_{18}$ alkyl monocarboxylic (fatty) acids and salts thereof. These fatty acids can be derived from animal and vegetable fats and oils, such as tallow, coconut oil and palm oil. Suitable saturated fatty acids can also be synthetically prepared (e.g., via the oxidation of petroleum or by hydrogenation of carbon monoxide via the Fisher-Tropsch process). Particularly preferred $C_{10}$–$C_{18}$ alkyl monocarboxylic acids are saturated coconut fatty acids, palm kernel fatty acids, and mixtures thereof.

Chelating Agents

The detergent compositions herein may also optionally contain one or more iron and manganese chelating agents. Such chelating agents can be selected from the group consisting of amino carboxylates, amino phosphonates, polyfunctionally-substituted aromatic chelating agents and mixtures thereof, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents in compositions of the invention have one or more, preferably at least two, units of the substructure

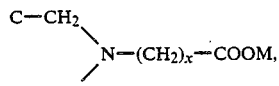

wherein M is hydrogen, alkali metal, ammonium or substituted ammonium (e.g. ethanolamine) and x is from 1 to about 3, preferably 1. Preferably, these amino carboxylates do not contain alkyl or alkenyl groups with more than about 6 carbon atoms. Operable amine carboxylates include ethylenediaminetetraacetates, N-hydroxyethylethylenediaminetriacetates, nitrilotriacetates, ethylenediamine tetraproprionates, triethylenetetraaminehexaacetates, diethylenetriaminepentaacetates, and ethanoldiglycines, alkali metal, ammonium, and substituted ammonium salts thereof and mixtures thereof.

Amino phosphonates are also suitable for use as chelating agents in the compositions of the invention when at least low levels of total phosphorus are permitted in detergent compositions. Compounds with one or more, preferably at least two, units of the substructure

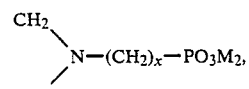

wherein M is hydrogen, alkali metal, ammonium or substituted ammonium and x is from 1 to about 3, preferably 1, are useful and include ethylenediaminetetrakis (methylenephosphonates), nitrilotris (methylenephosphonates) and diethylenetriaminepentakis (methylenephosphonates). Preferably, these amino phosphonates do not contain alkyl or alkenyl groups with more than about 6 carbon atoms. Alkylene groups can be shared by substructures.

Polyfunctionally-substituted aromatic chelating agents are also useful in the compositions herein. These materials comprise compounds having the general formula

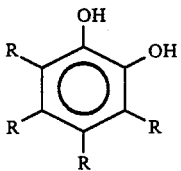

wherein at least one R is —SO₃H or —COOH or soluble salts thereof and mixtures thereof. U.S. Pat. No. 3,812,044, issued May 21, 1974, to Connor et al., incorporated herein by reference, discloses polyfunctionally-substituted aromatic chelating and sequestering agents. Preferred compounds of this type in acid form are dihydroxydisulfobenzenes and 1,2-dihydroxy-3,5-disulfobenzene or other disulfonated catechols in particular. Alkaline detergent compositions can contain these materials in the form of alkali metal, ammonium or substituted ammonium (e.g. mono- or triethanol-amine) salts.

If utilized, these chelating agents will generally comprise from about 0.1% to about 10% by weight of the detergent compositions herein. More preferably chelating agents will comprise from about 0.1% to about 3.0% by weight of such compositions.

Soil Release Agent

Polymeric soil release agents useful in the present invention include cellulosic derivatives such as hydroxyether cellulosic polymers, copolymeric blocks of ethylene terephthalate and polyethylene oxide or polypropylene oxide terephthalate, and cationic guar gums, and the like.

The cellulosic derivatives that are functional as soil release agents are commercially available and include hydroxyethers of cellulose such as Methocel ® (Dow) and cationic cellulose ether derivatives such as Polymer JR-124 ®, JR-400 ®, and JR-30M ® (Union Carbide). See also U.S. Pat. No. 3,928,213 to Temple et al., issued Dec. 23, 1975, which is incorporated by reference.

Other effective soil release agents are cationic guar gums such as Jaguar Plau ® (Stein Hall) and Gendrive 458200 (General Mills).

Preferred cellulosic soil release agents for use herein are selected from the group consisting of methyl cellulose; hydroxypropyl methylcellulose; hydroxybutyl methylcellulose; or a mixture thereof, said cellulosic polymer having a viscosity in aqueous solution at 20° C. of 15 to 75,000 centipoise.

A more preferred soil release agent is a copolymer having random blocks of ethylene terephthalate and polyethylene oxide (PEO) terephthalate. More specifically, these polymers are comprised of repeating units of ethylene terephthalate and PEO terephthalate in a mole ratio of ethylene terephthalate units to PEO terephthalate units of from about 25:75 to about 35:65, said PEO terephthalate units containing polyethylene oxide having molecular weights of from about 300 to about 2000. The molecular weight of this polymeric soil release agent is in the range of from about 25,000 to about 55,000. See U.S. Pat. No. 3,959,230 to Hays, issued May 25, 1976, which is incorporated by reference. See also U.S. Pat. No. 3,893,929 to Basadur issued July 8, 1975 (incorporated by reference) which discloses similar copolymers. Surprisingly, it has been found that these polymeric soil release agents balance the distribution of the fabric care agent of the present invention against a broad range of synthetic fabrics such as polyesters, nylons, polyester cotton blends and acrylics. This more uniform distribution of the fabric care agent can result in improved fabric care qualities.

Another preferred polymeric soil release agent is a crystallizable polyester with repeat units of ethylene terephthalate units containing 10–15% by weight of ethylene terephthalate units together with 90–80% by weight of polyoxyethylene terephthalate units, derived from a polyoxyethylene glycol of average molecular weight 300–5,000, and the mole ratio of ethylene terephthalate units to polyoxyethylene terephthalate units in the crystallizable polymeric compound is between 2:1 and 6:1. Examples of this polymer include the commercially available material Zelcon ® 5126 (from Dupont) and Milease ® T (from ICI).

The foregoing polymers and methods of their preparation are more fully described in European Patent Application 185,417, Gosselink, published June 25, 1986, which is incorporated herein by reference.

If utilized, these soil release agents will generally comprise from about 0.05% to about 5.0% by weight of the detergent compositions herein, more preferably soil release agents will comprise from about 0.2% to about 3.0% by weight of such compositions.

Clay Soil Removal/Anti-redeposition Agents

The detergent compositions of the present invention can also optionally contain from about 0.01% to about 5.0% by weight of water-soluble ethoxylated amines having clay soil removal and anti-redeposition properties. These compounds are selected from the group consisting of:

(1) ethoxylated monoamines having the formula:

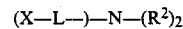

(2) ethoxylated diamines having the formula:

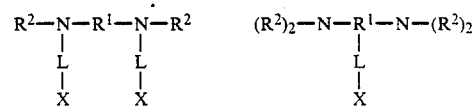

or

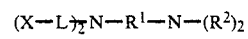

(3) ethoxylated polyamines having the formula:

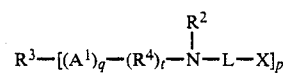

(4) ethoxylatd amine polymers having the general formula:

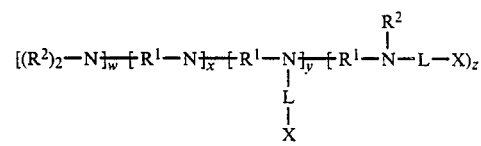

and (5) mixtures thereof; wherein A¹ is

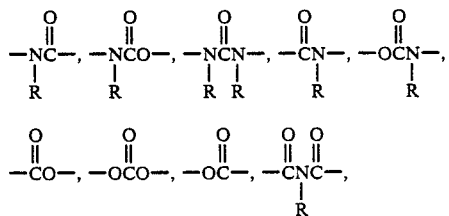

or —O—; R is H or $C_1$-$C_4$ alkyl or hydroxyalkyl; $R^1$ is $C_2$-$C_{12}$ alkylene, hydroxyalkylene, alkenylene, arylene or alkarylene, or a $C_2$-$C_3$ oxyalkylene moiety having from 2 to about 20 oxyalkylene units provided that no O—N bonds are formed; each $R^2$ is $C_1$-$C_4$ or hydroxyalkyl, the moiety —L—X, or two $R^2$ together form the moiety —$(CH_2)_4$, —$A^2$—$(CH_2)_s$—, wherein $A^2$ is —O— or —$CH_2$—, r is 1 or 2, s is 1 or 2, and r+s is 3 or 4; X is a nonionic group, an anionic group or mixture thereof; $R^3$ is a substituted $C_3$-$C_{12}$ alkyl, hydroxyalkyl, alkenyl, aryl, or alkaryl group having p substitution sites; $R^4$ is $C_1$-$C_{12}$ alkylene, hydroxyalkylene, alkenylene, arylene or alkarylene, or a $C_2$-$C_3$ oxyalkylene moiety having from 2 to about 20 oxyalkylene units provided that no O—O or O—N bonds are formed; L is a hydrophilic chain which contains the polyoxyalkylene moiety —$[(R^5O)_m(CH_2CH_2O)_n]$—, wherein $R^5$ is $C_3$-$C_4$ alkylene or hydroxyalkylene and m and n are numbers such that the moiety —$(CH_2CH_2O)_n$— comprises at least about 50% by weight of said polyoxyalkylene moiety; for said monoamines, m is from 0 to about 4, and n is at least about 12; for said diamines, m is from 0 to about 3, and n is at least about 6 when $R^1$ is $C_2$-$C_3$ alkylene, hydroxyalkylene, or alkenylene, and at least about 3 when $R^1$ is other than $C_2$-$C_3$ alkylene, hydroxyalkylene or alkenylene; for said polyamines and amine polymers, m is from 0 about 10 and n is at least about 3; p is from 3 to 8; q is 1 or 0; t is 1 or 0, provided that t is 1 when q is 1; w is 1 or 0; x+y+z is at least 2; and y+z is at least 2. The most preferred soil release and anti-redeposition agent is ethoxylated tetraethylenepentaimine.

Enzymes

Enzymes are a preferred optional ingredient and are incorporated in an amount of from about 0.025% to about 2%, preferably from about 0.05% to about 1.5% of the total composition. Preferred proteolytic enzymes should provide a proteolytic activity of at least about 5 Anson units (about 1,000,000 Delft units) per liter, preferably from about 15 to about 70 Anson units per liter, most preferably from about 20 to about 40 Anson units per liter. A proteolytic activity of from about 0.01 to about 0.05 Anson units per gram of product is desirable. Other enzymes, including amylolytic enzymes, are also desirably included in the present compositions.

Suitable proteolytic enzymes include the many species known to be adapted for use in detergent compositions. Commercial enzyme preparations such as "Savinase" and "Alcalase" sold by Novo Industries and "Maxatase" sold by Gist-Brocades, Delft, The Netherlands, are suitable. Other preferred enzyme compositions include those commercially available under the tradenames SP-72 ("Esperase") manufactured and sold by Novo Industries, A/S, Copenhagen, Denmark and "AZ-Protease" manufactured and sold by Gist-Brocades, Delft, The Netherlands.

Suitable amylases include "Rapidase" sold by Gist-Brocades and "Termamyl" sold by Novo Industries.

A more complete disclosure of suitable enzymes can be found in U.S. Pat. No. 4,101,457, Place et al., issued July 18, 1978, and in U.S. Pat. No. 4,507,219, Hughes, issued Mar. 26, 1985, both incorporated herein by reference.

Stabilizing System

Preferably, the liquid detergent compositions of the present invention contain a stabilizing agent to maintain the fabric care agent uniformly dispersed in the liquid detergent. Otherwise, density differences between the insoluble particles and the liquid base detergent can cause eventual particle settling or creaming.

The choice of the stabilizing agent for the present compositions depends upon factors such as the type and level of solvent ingredients in the composition.

Suitable suspending agents include various clay materials, such as montmorillonite clay, quaternized montmorillonite clays (e.g. Bentone 14, available from NL Industries), hectorites (e.g. Laponite S, available from LaPorte), polysaccharide gums (e.g. xanthan gum available from the Kelco Division of Merck & Co., Inc.), any of several long-chain acyl derivative materials or mixtures of such materials; diethanolamide of a long-chain fatty acid (e.g., PEG 3 lauramide), block polymers of ethylene oxide and propylene oxide (such as Pluronic F88 offered by BASF Wyandotte), sodium chloride, ammonium xylene sulfonate, sodium sulfate and polyvinyl alcohol. Other suspending agents found useful are alkanol amides of fatty acids, having from about 16 to about 22 carbon atoms, preferably from about 16 to about 18 carbon atoms. Preferred alkanol amides are stearic monoethanolamide, stearic diethanolamide, stearic monoisopropanolamide and stearic monoethanolamide stearate. Other long-chain acyl derivatives include long-chain esters of long-chain alkanol amides (e.g., stearamide DEA distearate, stearamide MEA stearate).

The most preferred suspending agent for use in the present invention is the quaternized montmorillonite clay.

This suspending agent is present at a level of from about 0.1% to about 10.0%, preferably from about 0.3% to about 1.5%.

Other Optional Detergent Ingredients

Other optional ingredients which can be included in detergent compositions of the present invention, in their conventional art-established levels for use (generally from 0 to about 20%), include solvents, hydrotropes, solubilizing agents, suds suppressors, processing aids, soil-suspending agents, corrosion inhibitors, dyes, fillers, optical brighteners, germicides, pH-adjusting agents (monoethanolamine, sodium carbonate, sodium hydroxide, etc.), enzyme-stabilizing agents, bleaches, bleach activators, perfumes, and the like. A particularly preferred optional ingredient for use in granular detergents is from about 4% to about 15% of a smectite clay for softening benefits.

DETERGENT COMPOSITIONS

1. Granular Detergent

Granular detergent compositions embodying the present invention can be formed by conventional techniques, i.e., by slurrying the individual components (with the exception of the ion-pair/wax composites) in water and then atomizing and spray-drying the resultant mixture, or by pan or drum agglomeration of the ingredients. The ion-pair/wax composites can then be added directly into the composition.

2. Laminated Thru-the-Wash Laundry Products

Compositions of this invention can also be adapted to a thru-the-wash, compact, laminated laundry product which comprises powdered laundry actives laminated between two plies, at least one ply of which is a strong wet-strength, high stretch paper tissue having one or a multiplicity of deeply embossed (stretched) non-connecting tissue cup-like depressions containing the powder active with the other ply covering the cups. The plies are sealed with a glue pattern around the cup rims. The high stretch paper is made to withstand an embossed stretch to form said deeply embossed (stretched) cups and to survive the rigors of a washing machine. This form of thru-the-wash laundry product is fully described in U.S. Pat. No. 4,638,907 to Bedenk et al., issued Jan. 27, 1987, which is incorporated by reference herein. This pouch can contain the conditioning active alone, or in combination with surfactants and/or other laundry actives (e.g., smectite clay for textile softening).

The paper used in the laminated laundry product must have certain physical characteristics. It must have multi-directional strength as well as multi-directional stretch (elongation potential) to allow the product of this invention to be made in the first place and to allow the product to withstand the rigors of practical use. Specifically, the paper must have a dry MD tensile strength of from about 1,200 to about 2,400 grams per inch, preferably at least about 1,400 grams per inch, with from about 30% to about 60% stretch, preferably at least about 45% as defined hereinbelow. It must have a dry CD tensile strength of from about 700 to about 1,500 grams per inch, preferably at least about 800 grams per inch, with from about 9 to about 25% stretch, preferably at least about 12%.

The requisite strength of the paper can be obtained through the use of various additives commonly used in papermaking. Examples of useful additives include wet strength agents such as urea-formaldehyde resins, melamine formaldehyde resins, polyamide-epichlorohydrin resins, polyethyleneimine resins, polyacrylamide resins, and dialdehyde starches. Dry strength additives, such as polysalt coacervates rendered water insoluble by the inclusion of ionization suppressors, are also useful herein. Complete descriptions of useful wet strength agents can be found in TAPPI Monograph Series No. 29, "Wet Strength Resin in Paper and Paper Board," Technical Association of the Pulp and Paper Industry (New York 1965), incorporated herein by reference, and in other common references.

One specific paper found particularly useful in the present invention is the tissue paper described by Trokhan in U.S. Pat. No. 4,529,480, issued July 16, 1985, incorporated herein by reference.

The conditioning agents and/or the laundry actives are then laminated into the cells of the laundry product as described in U.S. Pat. No. 4,638,907, to Bedenk et al., already incorporated herein by reference. These conditioning agents and/or the laundry actives can also be adapted for use in a dissolvable laundry product; such as a dissolveable pouch.

3. Liquid Detergents

Liquid compositions of the present invention can contain water and other solvents. Small quantities of low molecular weight primary or secondary alcohols, exemplified by methanol, ethanol, propanol, and isopropanol are suitable. However, care must be taken so as not to dissolve the ion-pair/wax composite. Monohydric alcohols are preferred for solubilizing the surfactant, but polyols containing from about 2 to about 6 carbon atoms and from about 2 to about 6 hydroxy groups can be used and can provide improved enzyme stability (if enzymes are included in the composition). Examples of polyols include propylene glycol, ethylene glycol, and glycerine. Propylene glycol is particularly preferred.

In preferred executions of the invention, the product should desirably be free-flowing across a reasonable temperature range.

The detergent compositions of the invention are particularly suitable for laundry use, but are also suitable for cleaning hard surfaces and for dishwashing.

In a laundry method aspect of the invention, typical laundry wash water solutions comprise from about 0.1% to about 2% by weight of the detergent compositions of the invention. Fabrics to be laundered are agitated in these solutions to effect cleaning, stain removal, and fabric care benefits. The pH of a 0.1% by weight aqueous solution of this composition will be in the range of from about 6.0 to about 11.0, and most preferably from about 7.0 to about 10.0.

4. Shampoos

Compositions of this invention also can be formulated in a shampoo form. The shampoos comprise from about 1% to about 60% of the static care agent; from about 5% to about 60% of a synthetic surfactant; and the balance water. Suitable surfactants which have been fully described above include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, monoethanolamine cocoyl sulfate, monoethanolamine lauroyl sulfate, sodium tridecyl benzene sulfonate and sodium dodecyl benzene sulfonate.

These shampoos can contain a variety of nonessential optional components. Such conventional optional ingredients are well known to those skilled in the art, e.g., preservatives, such as benzyl alcohol, ethyl paraben, propyl paraben and imidazolidinyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as a diethanolamide of a long-chain fatty acid (e.g. PEG 3 lauramide), block polymers of ethylene oxide and propylene oxide, sodium chloride, sodium sulfate, polyvinyl alcohol, and ethyl alcohol; pH adjusting agents, such as citric acid, succinic acid, phosphoric acid, sodium hydroxide, sodium carbonate; perfumes; dyes; and, sequestering agents, such as disodium ethylenediamine tetraacetate. Such agents generally are used individually at a level of from about 0.01% to about 10%, preferably from about 0.5% to about 5.0% by weight of the composition.

The conditioning agents of the present invention can also be used in combination with other carriers. A more detailed description of such forms follows:

1. Dryer-release Sheets

Compositions of this invention can also be adapted to an article of manufacture for use in providing fabric care benefits in an automatic laundry dryer comprising the ion-pair/wax composite of the present invention along with a dispensing means which provides for release of an effective amount of said composition to fabrics in the dryer at automatic dryer operating temperatures.

When the dispensing means is a flexible substrate in sheet configuration the fabric conditioning composition is releasably affixed on the substrate to provide a weight ratio of fabric conditioning composition to dry substrate ranging from about 10:1 to about 0.25:1, preferably from about 5:1 to about 1:1. Ion-pair wax composites having different melting points can be obtained by changing the mole ratio of the amines to surfactant and/or by changing the alkyl chain length of either the amines or the surfactant or both or changing the wax identity or ion-pair:wax ratio, as described above. This ability to tailor the melting points of the ion-pair/wax composites is important for dryer-added compositions to provide fabric conditioning benefits. The most preferred fabric conditioning agents are solid at room temperature, have a softening phase transition temperature at or above about 30° C., and become a flowable liquid below about 100° C., preferably below 90° C. A fabric conditioning agent which is solid at room temperature is desirable in order to keep the dryer-added composition from having a tacky feel, while its softening and fluidity at high temperatures facilitate the substrate coating process and the subsequent fabric conditioning active transfer from fabric conditioning sheet to fabrics in the clothes dryer. These dryer-added compositions can also contain a variety of non-essential optional components. Such optional ingredients are well known to those skilled in the art, e.g., polymeric soil release agents which include hydroxyether cellulosic polymers, block co-polymers of polyethylene terephthalate and polyoxyethylene terephthalate, block co-polymers of polyethylene phthalate and polyethylene glycol, and cationic guar gums, and the like. A particularly preferred polymeric soil release agent is disclosed in European patent application 185,417, Gosselink, published June 25, 1986 incorporated herein by reference. Examples of other optional fabric softening agents are the compositions described in U.S. Pat. No. 4,103,047, Zaki et al., issued July 25, 1978, U.S. Pat. No. 4,237,155, Kardouche, issued Dec. 2, 1980; U.S. Pat. No. 3,686,025, Morton, issued Aug. 22, 1972; U.S. Pat. No. 3,849,435, Diery et al., issued Nov. 19, 1974 and U.S. Pat. No. 4,017,996, Bedenk, issued Feb. 14, 1978, said patents are hereby incorporated herein by reference. Such optional components include anti-creasing agents, finishing agents, fumigants, lubricants, fungicides, and sizing agents. The amount of these additives will generally comprise from about 0.1% to about 10% by weight of the fabric conditioning agent.

The fabric conditioning compositions can be employed by simply adding a measured amount into the dryer, e.g., as a liquid dispersion or as free-flowing prills. However, in a preferred embodiment, the fabric conditioners are provided as an article of manufacture in combination with a dispensing means such as a flexible substrate which effectively releases the composition in an automatic clothes dryer. Such dispensing means can be designed for single usage or for multiple uses.

The devices and articles suitable for dispensing the fabric conditioning composition into automatic dryers include those described in U.S. Pat. Nos. 4,103,047, Zaki et al., issued July 25, 1978; 3,736,668, Dillarstone, issued June 5, 1973; 3,701,202, Compa et al., issued Oct. 31, 1972; 3,634,947, Furgal, issued Jan. 18, 1972; 3,633,538, Hoeflin, issued Jan. 11, 1972; and 3,435,537, Rumsey, issued Apr. 1, 1969. All of these patents are incorporated herein by reference.

A highly preferred article herein comprises the fabric conditioning composition releasably affixed to a flexible substrate in a sheet configuration. Highly preferred paper, woven or nonwoven "absorbent" substrates useful herein are fully disclosed in Morton, U.S. Pat. No. 3,686,026, issued Aug. 22, 1972, incorporated herein by reference. It is known that most substances are able to absorb a liquid substance to some degree; however, the term "absorbent" as used herein, is intended to mean a substance with an absorbent capacity (i.e., a parameter representing a substrate's ability to take up and retain a liquid) from about 4 to about 12, preferably about 5 to about 7, times its weight of water.

The conditioning agents of the present invention can also be applied to the laminated sheets described above, added during the wash, and carried over to the dryer. The conditioning agent is then released during the drying process. It is preferred that the ion-pair/wax composite have a melting point of above about 54° C. to prevent melting during the wash cycle and allow release in the dryer.

2. Aqueous Dispersions

The ion-pair/wax composites of this invention are well adapted for direct application to fibers or fabrics and as such can also be formulated as aqueous dispersions.

The aqueous dispersion in an aerosol form comprises from about 2% to about 60% of the ion-pair/wax composite of the present invention; from about 10% to 50% water; from about 10 to about 30% of a suitable organic solvent; the balance being a suitable propellant. Examples of such propellants are the chlorinated, fluorinated and chlorofluorinated lower molecular weight hydrocarbons. Nitrous oxide, carbon dioxide, isobutane and propane may also be used as propellant gases. These propellants are used at a level sufficient to expel the contents of the container. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, diethyl tartrate, butanediol, and mixtures thereof.

The ion-pair wax composites of the present invention are also useful as aqueous dispersions added to the wash or rinse.

When it is desired to utilize such ion-pair/wax composites for use in domestic laundering, it is necessary that they be delivered from particles with an average particle diameter as described hereinabove. That is, they preferably have an average particle diameter from about 1 to about 1000 nanometers, preferably about 20 to 500 nanometers for rinse-added dispersions and 10 to 300 microns, most preferably about 10 to 150 microns for wash-added dispersions. The balance of the composition comprises a liquid carrier, preferably the carrier is water or a mixture of water and monohydric alcohols.

Other optional components of these liquid conditioning compositions of this type are conventional in nature, and generally comprise from about 0.1% to about 20% by weight of the composition. Such optional components for fabric conditioners include, but are not limited to, colorants, perfumes, bacterial inhibitors, optical brighteners, opacifiers, viscosity modifiers, fabric absorbency boosters, emulsifiers, stabilizers, shrinkage controllers, spotting agents, germicides, fungicides, anti-corrosion agents and the like.

The pH of the rinse-added fabric softener compositions of this invention is not critical and may be anywhere in the normal range (i.e., a pH of from about 5 to about 7) for conventional fabric conditioning compositions.

The liquid fabric conditioning compositions of the present invention can be prepared by conventional methods. Suitable methods for preparing these compositions are described in the aforementioned U.S. patents.

EXAMPLES

The following examples illustrate the present invention. The abbreviations used are:

| Code | Ingredient |
| --- | --- |
| $C_{13}$HLAS | $C_{13}$ linear alkylbenzene sulfonic acid |
| $C_{11.4}$HLAS | $C_{11.4}$ linear alkylbenzene sulfonic acid |
| NI 23-6.5T | $C_{12-13}$ alkyl polyethoxylate (6.5 T) available as Neodol 23-6.5T from Shell T = stripped of lower ethoxylated fractions and fatty alcohol |
| NI 25-8T | $C_{12}$-$C_{15}$ alkyl polyethoxylate (8T) |
| stabilizer | Bentone-14 quaternized montmorillonite clay obtained from NL Industries |
| DTPA | diethylenetriaminepentaacetate |
| PPT | poly(terephthalate propyleneglycol ester) ethoxylated with about 30 moles of ethylene oxide |
| DTA/$C_8$ HLAS/ paraffin - micro blend | a composite formed from ditallow amine, $C_8$HLAS, a parraffin wax (Boler 1014, sold by Bareco) and a hard microcrystalline wax (BE Square 195, sold by Bareco) in a ratio of 33:17:30:20 |
| DTA/$C_3$ HLAS/ paraffin | a composite formed from ditallow amine, $C_3$HLAS and paraffin wax (Boler 1014) in a ratio of 54:21:25 |
| TEPA-E$_{15-18}$ | tetraethylenepentaimine ethoxylated with 15–18 moles (avg.) of ethylene oxide at each hydrogen site on each nitrogen |
| ETPG | ethylene terephthalate-polyoxyethylene glycol copolymer (Zelcon 4780 sold by E.I. duPont as a 15% dispersion in water). Dried Zelcon 4780 is the dehydrated dispersion dried in a thin film at approximately 100° C. Zelcon 4780 is also described herein in the section entitled "Polymeric Soil Release Agent." |
| SMS | sorbitanmonostearate |
| Clay | Bentolite L, a montmorillonite clay, obtained from Southern Clay Products |
| Misc | enzyme stabilizers, other phase stabilizers, perfumes, brighteners, dyes, water, other solvents, pH adjusting agents, e.g., monoethanolamine, diethanolamine, triethanolamine, KOH, NaOH, NH$_4$OH and salts. |

EXAMPLE I

This example demonstrates the synthesis of a ditallow aminelinear $C_3$ alkylbenzene sulfonate/paraffin wax composite.

An ion-pair complex is formed by combining a 1:1 molar ratio of hydrogenated ditallow amine (available from Sherex Corporation, Dublin, Ohio as Adogen ® 240) and cumene sulfonic acid. The acid is added to a 70° C. to 150° C. melt of the amine with agitation to give a homogeneous fluid. The mixture is then cooled, with stirring, to room temperature. The resulting ion-pair complex is then mixed in a 3 to 1 weight ratio of ion-pair complex to paraffin wax (Boler 1014, melting point 161°–165° F. (72°–74° C.). N-paraffins=58%, isoparaffins=42%. Penetration=13 at 77° F. (25° C.)). The resulting mixture is again heated with agitation to give a homogeneous fluid.

The resulting composite can be applied directly to fabrics to produce conditioning benefits or can be incorporated into a variety of carriers such as laundry detergents, washer- or dryer-added sheets, rinse added solutions, or shampoos in order to impart the desired conditioning benefits.

Substantially similar results can be obtained when the ion-pair complex is replaced, in whole or in part, with an equivalent amount of ditallow amine (hydrogenated or unhydrogenated) complexed with a linear $C_1$-$C_{20}$ alkylbenzene sulfonate (LAS),
ditallow methyl (hydrogenated or unhydrogenated) amine complexed with a $C_1$-$C_{20}$ LAS,
dipalmityl amine complexed with a $C_1$-$C_{20}$ LAS,
dipalmityl methyl amine complexed with a $C_1$-$C_{20}$ LAS,
distearyl amine complexed with a $C_1$-$C_{20}$ LAS,
distearyl methyl amine complexed with a $C_1$-$C_{20}$ LAS,
diarachidyl amine complexed with a $C_1$-$C_{20}$ LAS,
diarachidyl methyl amine complexed with a $C_1$-$C_{20}$ LAS,
palmityl stearyl amine complexed with a $C_1$-$C_{20}$ LAS,
palmityl stearyl methyl amine complexed with a $C_1$-$C_{20}$ LAS,
palmityl arachidyl amine complexed with a $C_1$-$C_{20}$ LAS,
palmityl arachidyl methyl amine complexed with a $C_1$-$C_{20}$ LAS,
stearyl arachidyl amine complexed with a $C_1$-$C_{20}$ LAS,
stearyl arachidyl methyl amine complexed with a $C_1$-$C_{20}$ LAS,
ditallow amine (hydrogenated or unhydrogenated) complexed with a $C_1$-$C_{20}$ alkyl sulfonate (AS),
ditallow methyl amine (hydrogenated or unhydrogenated) complexed with a $C_1$-$C_{20}$ AS,
dipalmityl amine complexed with a $C_1$-$C_{20}$ AS,
dipalmityl methyl amine complexed with a $C_1$-$C_{20}$ AS,
distearyl amine complexed with a $C_1$-$C_{20}$ AS,
distearyl methyl amine complexed with a $C_1$-$C_{20}$ AS,
diarachidyl amine complexed with a $C_1$-$C_{20}$ AS,
diarachidyl methyl amine complexed with a $C_1$-$C_{20}$ AS,
palmityl stearyl amine complexed with a $C_1$-$C_{20}$ AS,
palmityl stearyl methyl amine complexed with a $C_1$-$C_{20}$ AS,
palmityl arachidyl amine complexed with a $C_1$-$C_{20}$ AS,
palmityl arachidyl methyl amine complexed with a $C_1$-$C_{20}$ AS,
stearyl arachidyl amine complexed with a $C_1$-$C_{20}$ AS, stearyl arachidyl methyl amine complexed with a $C_1$–$C_{20}$ AS,
ditallow amine (hydrogenated or unhydrogenated) complexed with an aryl sulfonate,
ditallow methyl amine (hydrogenated or unhydrogenated) complexed with an aryl sulfonate,
dipalmityl amine complexed with an aryl sulfonate,
dipalmityl methyl amine complexed with an aryl sulfonate,
distearyl amine complexed with an aryl sulfonate,
distearyl methyl amine complexed with an aryl sulfonate,
diarachidyl amine complexed with an aryl sulfonate,
diarachidyl methyl amine complexed with an aryl sulfonate,
palmityl stearyl amine complexed with an aryl sulfonate,
palmityl stearyl methyl amine complexed with an aryl sulfonate,
palmityl arachidyl amine complexed with an aryl sulfonate,
palmityl arachidyl methyl amine complexed with an aryl sulfonate,
stearyl arachidyl amine complexed with an aryl sulfonate, and mixtures of these ion-pair complexes and
stearyl arachidyl methyl amine complexed with an aryl sulfonate,
and mixtures of these ion-pair complexes.

Substantially similar results can also be obtained when the paraffin wax is replaced, in whole or in part, with an equivalent amount of a microcrystalline wax or a paraffin/microcrystalline wax blend.

EXAMPLE II

This example demonstrates the synthesis of a ditallow amine-linear $C_8$ alkylbenzene sulfonate/paraffin-microcrystalline wax composite.

An ion-pair complex is formed as described above in Example I, substituting linear $C_8$ benzene sulfonic acid for the cumene sulfonic acid.

The resulting ion-pair complex is then mixed in a 5:3:2 weight ratio of ion-pair complex:paraffin wax (Boler 1014):microcrystalline wax (BE Square 195, available from Bareco Corp.). The resulting mixture is heated with agitation to give a homogeneous fluid.

The resulting composite can be applied directly to fabrics to produce conditioning benefits, or can be incorporated into any of a variety of carriers such as laundry detergents, washer- or dryer-added sheets, rinse-added solutions or shampoos in order to impart the desired conditioning benefits.

EXAMPLE III

Liquid detergent compositions of the present invention are as follows.

The following compositions are prepared by adding the components to a mixing tank in the order listed with continuous mixing.

| Detergent Base Components | Wt. % A | B |
|---|---|---|
| $C_{11.4}$HLAS | 17.2 | 18.0 |
| NI 25-8T | — | 7.0 |
| NI 23-6.5T | 8.7 | — |
| propanediol | 14.49 | — |
| monoethanolamine | 1.93 | — |
| $C_{8-15}$ alkenyl succinate | 11.21 | — |
| sodium citrate | 3.48 | 10.0 |
| DTPA | 0.29 | — |
| TEPA-$E_{15-18}$ | 1.45 | — |
| PPT | 0.97 | 1.0 |
| protease enzyme (2.0 AU/g) | 0.58 | 0.6 |
| amylase enzyme (375 Amylase Units/g) | 0.30 | 0.3 |
| stabilizer | 0.72 | 0.7 |
| miscellaneous and water | balance to 100% | |

The ion-pair/wax composite of Example II is frozen by liquid nitrogen and then ground in an Oster® blender pulsematic Model 16 for about 60 seconds. The ground particles are then sieved through a 500 micron screen. The particle size of the fraction ranges from about 10 microns to about 500 microns (as determined by, for example, a Malvern® 2600 particle size analyzer). While still frozen, 10 parts of the particles are then added to 90 parts of the detergent base and the resulting detergent composition is mixed by a high shear mechanical dispersing probe (e.g. a Polytron Model PT 10/35 obtained from Brinkman Instruments) in order to insure even distribution of the particles and to further reduce the average particle size diameter to about 80 microns.

The resulting detergent compositions exhibit excellent cleaning and excellent fabric care benefits such as softening and static control.

Substantially similar results are obtained when the hydrogenated ditallow amine-$C_8$HLAS ion-pair complex is replaced, in whole or in part, with an equivalent amount of
ditallow amine (hydrogenated or unhydrogenated) complexed with a linear $C_1$–$C_{20}$ alkylbenzene sulfonate (LAS),
ditallow methyl amine (hydrogenated or unhydrogenated) complexed with a $C_1$–$C_{20}$ LAS,
dipalmityl amine complexed with a $C_1$–$C_{20}$ LAS,
dipalmityl methyl amine complexed with a $C_1$–$C_{20}$ LAS,
distearyl amine complexed with a $C_1$–$C_{20}$ LAS,
distearyl methyl amine complexed with a $C_1$–$C_{20}$ LAS,
diarachidyl amine complexed with a $C_1$–$C_{20}$ LAS,
diarachidyl methyl amine complexed with a $C_1$–$C_{20}$ LAS,
palmityl stearyl amine complexed with a $C_1$–$C_{20}$ LAS,
palmityl stearyl methyl amine complexed with a $C_1$–$C_{20}$ LAS,
palmityl arachidyl amine complexed with a $C_1$–$C_{20}$ LAS,
palmityl arachidyl methyl amine complexed with a $C_1$–$C_{20}$ LAS,
stearyl arachidyl amine complexed with a $C_1$–$C_{20}$ LAS,
stearyl arachidyl methyl amine complexed with a $C_1$–$C_{20}$ LAS,
ditallow amine (hydrogenated or unhydrogenated) complexed with a $C_1$–$C_{20}$ alkyl sulfonate (AS),
ditallow methyl amine (hydrogenated or unhydrogenated) complexed with a $C_1$–$C_{20}$ AS,
dipalmityl amine complexed with a $C_1$–$C_{20}$ AS,
dipalmityl methyl amine complexed with a $C_1$–$C_{20}$ AS,
distearyl amine complexed with a $C_1$–$C_{20}$ AS,
distearyl methyl amine complexed with a $C_1$–$C_{20}$ AS,
diarachidyl amine complexed with a $C_1$–$C_{20}$ AS,
diarachidyl methyl amine complexed with a $C_1$–$C_{20}$ AS,
palmityl stearyl amine complexed with a $C_1$–$C_{20}$ AS,
palmityl stearyl methyl amine complexed with a $C_1$–$C_{20}$ AS, palmityl arachidyl amine complexed with a $C_1$–$C_{20}$ AS,
palmityl arachidyl methyl amine complexed with a $C_1$–$C_{20}$ AS,
stearyl arachidyl amine complexed with a $C_1$–$C_{20}$ AS,
stearyl arachidyl methyl amine complexed with a $C_1$–$C_{20}$ AS,
ditallow amine (hydrogenated or unhydrogenated) complexed an aryl sulfonate,
ditallow methyl amine (hydrogenated or unhydrogenated) complexed with an aryl sulfonate,
dipalmityl amine complexed with an aryl sulfonate,
dipalmityl methyl amine complexed with an aryl sulfonate,
distearyl amine complexed with an aryl sulfonate,
distearyl methyl amine complexed with an aryl sulfonate,
diarachidyl amine complexed with an aryl sulfonate,
diarachidyl methyl amine complexed with an aryl sulfonate,
palmityl stearyl amine complexed with an aryl sulfonate,
palmityl stearyl methyl amine complexed with an aryl sulfonate,
palmityl arachidyl amine complexed with an aryl sulfonate, and
palmityl arachidyl methyl amine complexed with an aryl sulfonate,
stearyl arachidyl amine complexed with an aryl sulfonate, and
stearyl arachidyl methyl amine complexed with an aryl sulfonate,
and mixtures of these ion-pair complexes.

Substantially similar results are also obtained when the paraffin/microcrystalline wax blend is replaced, in whole or in part, with an equivalent amount of a microcrystalline wax, a paraffin wax or mixtures thereof.

More preferred are complexes formed from the combination of ditallow amine (hydrogenated or unhydrogenated) or ditallow methyl amine (hydrogenated or unhydrogenated) complexed with $C_1$–$C_{20}$ alkylaryl sulfonate or an aryl sulfonate. Even more preferred are those complexes formed from hydrogenated ditallow amine complexed with a $C_1$–$C_{13}$ LAS or a benzene sulfonate. Most preferred are complexes formed from hydrogenated ditallow amine complexed with $C_2$–$C_8$ LAS.

EXAMPLE IV

An aerosol spray is prepared by combining the following ingredients:

| Ingredient | Percent (wt) |
| --- | --- |
| Ion-pair/wax composite | 20% |
| Propylene glycol | 20% |
| Propane | 20% |
| Water | 40% |

The ion-pair/wax composite of Example I is combined with the propylene glycol and water. These components are then added to the propane. Application of the resulting aerosol spray will condition fabrics.

EXAMPLE V

A shampoo composition of the present invention is made by combining the following components:

| Ingredient | Percent (wt) |
| --- | --- |
| Ion-pair/wax composite | 10.0% |
| Ammonium lauryl sulfate | 12.0% |
| Ammonium xylene sulfonate | 2.2% |
| Ammonium laureth sulfate | 4.0% |
| NaCl | 0.5% |
| Perfume and minor ingredients | 1.2% |
| Water | Balance up to 100% |

5 g of the ion-pair/wax composite of Example I is added to a surfactant mixture containing 12.0 g of ammonium lauryl sulfate, 4.0 g of ammonium laureth sulfate and 2.2 g ammonium xylene sulfonate, the balance of the components are added and the resulting mixture is agitated in the Tekmar ® Mill set at 70 for 2 minutes at 70° C.

1 g of the resulting shampoo composition is added to hair which had been wetted with water, worked through the hair and then rinsed out. The washed hair is clean and exhibits reduced electrostatic charge (which causes "fly-away" hair), improved wet and dry combing, softness and manageability.

Substantially similar results are obtained when the surfactant mixture of ammonium lauryl sulfate, and ammonium laureth sulfate is replaced, in whole or in part, with an equivalent amount of any of the following surfactants used individually or in mixtures; potassium lauryl sulfate, potassium laureth sulfate, sodium lauryl sulfate, sodium laureth sulfate, triethanolamine lauryl sulfate, triethanolamine laureth sulfate, sodium tridecyl benzene sulfonate sodium dodecyl benzene sulfonate, or mixtures thereof.

EXAMPLE VI

Liquid detergent compositions of the present invention are as follows:

| Component | Wt. % A | Wt. % B |
| --- | --- | --- |
| $C_{13}$ linear alkylbenzene sulfonic acid | 7.2 | 7.2 |
| $C_{14-15}$ alkyl polyethoxylate (2.25) sulfuric acid | 10.8 | 10.8 |
| $C_{12-13}$ alcohol polyethoxylate (6.5)* | 6.5 | 6.5 |
| $C_{12}$ alkyl trimethylammonium chloride | 1.2 | 0.6 |
| $C_{12-14}$ fatty acid | 1.30 | — |
| Oleic acid | 2.0 | — |
| Palm kernel fatty acid (stripped) | — | 15.0 |
| Citric acid (anhydrous) | 4.0 | 4.0 |
| Diethylenetriamine pentaacetic acid | 0.23 | 0.23 |
| Protease enzyme (2.0 AU/g) | 0.75 | 0.75 |
| Amylase enzyme (375 Amylase Units/g) | 0.16 | 0.16 |
| TEPA-$E_{15-18}$** | 1.5 | 1.5 |
| Monoethanolamine | 2.0 | — |
| (moles of alkanolamine) | (0.033) | (0) |
| Sodium ion | 1.66 | 2.75 |
| Potassium ion | 2.65 | 2.55 |
| (molar K+:Na+) | (0.94) | (0.55) |
| Propylene glycol | 6.8 | 5.0 |
| Ethanol | 7.8 | 8.5 |
| Formic acid | 0.66 | 0.66 |
| Stabilizer | 0.75 | 0.75 |
| Calcium ion | 0.03 | 0.03 |
| Ion-pair/wax composite (DTA/$C_8$ HLAS/paraffin-micro blend) | 10.0 | — |
| Ion-pair/wax composite (DTA/$C_3$ HLAS/paraffin) | — | 6.7 |
| Minors and water | Balance to 100 | |
| pH at concentration of 10% | 8.65 | 8.5 |

-continued

| Component | Wt. % | |
|---|---|---|
| | A | B |
| in water at 68° F. (20° C.) | | |

*Alcohol and monoethoxylated alcohol removed
**Tetraethylene pentaimine ethoxylated with 15-18 moles (avg.) of ethylene oxide at each hydrogen site Composition A is prepared by adding the components, with continuous mixing, in the following order: paste premix of alkylbenzene sulfonic acid, sodium hydroxide, propylene glycol and ethanol; paste premix of alkyl polyethoxylate sulfuric acid, sodium hydroxide and ethanol; pentaacetic acid; alcohol polyethoxylate; premix of water, brighteners, alkanolamine, and alcohol polyethoxylate; ethanol; sodium and potassium hydroxide; fatty acid, citric acid; formic acid and calcium; alkyl trimethylammonium chloride; TEPA-$E_{15-18}$; adjust pH to about 8.1; stabilizer; balance of components and ion-pair/wax composite.

Composition B is prepared by adding the components, with continuous mixing, in the following order: paste premix of alkyl polyethoxylate sulfuric acid and ethanol; 2.5 parts water; propylene glycol; premix of ethanol and brightener; ethanol; premix of water, propylene glycol and brightener; alcohol polyethoxylate; sodium hydroxide; potassium hydroside; fatty acid; alkylbenzene sulfuric acid; premix of citric acid and calcium; pentaacetic acid; formic acid; alkyl trimethylammonium chloride; TEPA-$E_{15-18}$; potassium hydroxide, water; stabilizer; balance of components and ion-pair wax composite.

The detergent compositions exhibit excellent cleaning and excellent fabric care benefits such as softening and static control.

EXAMPLE VII

This example demonstrates a dryer-added sheet of the present invention.

| Fabric Conditioning Composition Components | Wt. % |
|---|---|
| ETPG | 37.0 |
| SMS | 10.0 |
| Ion-pair/wax composite | 46.0 |
| Clay | 6.0 |
| Perfume | 1.0 |
| Dryer-added Sheet Substrate Composition | |
| Rayon fibers | 70 |
| Polyvinyl acetate | 30 |
| (10" × 14" sheets, 1.4 gm) | |

The ion-pair/wax composite of Example II is co-melted under agitation with soil release polymer, sorbitanmonostearate, clay, and perfume until a constant viscosity is achieved. The substrate (made of the rayon fibers with polyvinyl acetate) is then coated with about 4 grams of the molten actives and dried overnight. This provides a weight ratio of fabric conditioning composition:dry substrate of approximately 3.

Following solidification of the fabric conditioning composition, the substrate is slit with a knife, said slits being in substantially parallel relationship and extending to within about 1 inch from at least one edge of said substrate. The width of an individual slit is approximately 0.2 inches. These dryer added sheets are added to a clothes dryer together with damp fabrics to be treated. The heat and tumbling action of the revolving dryer drum evenly distributes the composition over all fabrics, and dries the fabrics. The dryer added sheets exhibit excellent fabric care benefits such as softening, static control, and soil release.

EXAMPLE VIII

A liquid fabric or fiber softener is prepared by combining the following ingredients:

| Ingredients | Percent (wt) |
|---|---|
| Ion-pair/wax composite of Example II (500 nm) | 30% |
| Water | 60% |
| Minor ingredients | 10% |

Application of 5 g of the resulting conditioner provides conditioning benefits to fabrics and/or to fibers, such as hair.

EXAMPLE IX

A granular laundry detergent composition of the present invention is made as follows:

The following components are combined and then spray dried in a conventional manner to form detergent premix.

| Ingredient | Percent Weight |
|---|---|
| $C_{13}$HLAS | 7.0% |
| Sodium $C_{14}$-$C_{15}$ alkyl sulfate | 7.0% |
| Sodium tripolyphosphate | 28.7% |
| NI 23-6.5T | 1.1% |
| DTPA | 1.1% |
| Sodium silicate (1.6 r) | 10.9% |
| Sodium carbonate | 20.6% |
| Water and Minors and Misc. ingredients | Balance to 100% |

10 parts of the ion-pair/wax composite of Example I (with an average particle size of 80 microns) and 5 parts of a sodium montmorillonite clay are added to 85 parts of the pre-mix and the resulting detergent composition is thoroughly mixed to insure even distribution.

The resulting detergent composition exhibits excellent cleaning and excellent fabric care benefits such as softness and static control.

What is claimed is:

1. A detergency composition comprising:
  A. from about 1% to about 98% of a water-soluble detergent surfactant selected from the group consisting of cationic surfactants, nonionic surfactants, zwitterionic surfactants, amphoteric surfactants and anionic surfactants and mixtures thereof;
  B. from about 0.1% to about 20% of a water-insoluble composite having an average diameter of from about 10 to about 300 microns, comprising (i) from about 1 to about 99% of an alkyl amine-anionic surfactant ion-pair complex having the formula:

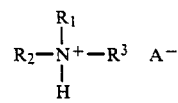

wherein each $R_1$ and $R_2$ independently is $C_{16}$ to $C_{20}$ alkyl or alkenyl, $R_3$ is H or $CH_3$, and A is an anionic surfactant selected from the group consisting of alkyl sulfonates, aryl sulfonates, alkylaryl sulfonates, alkyl sulfates, dialkyl sulfosuccinates, alkyl oxybenzene sulfonates, acyl isethionates, acylalkyl taurates, olefin sulfonates, alkyl ethoxylated sulfates and paraffin sulfonates, and mixtures of such ion-pair complexes; and (ii) from about 99% to about 1% of a nonsilicone wax; and C. from about 5% to about 50% of a detergency builder other than $C_{10}$–$C_{18}$ alkyl monocarboxylic acids or salts thereof.

2. A detergency composition agent according to claim 1 wherein said ion-pair/wax composites have an average diameter of from about 10 to about 250 microns.

3. A detergency composition according to claim 2 wherein A is selected from the group consisting of linear $C_1$–$C_{20}$ alkyl sulfonates, linear $C_1$ to $C_{20}$ alkylaryl sulfonates, $C_{12}$ to $C_{18}$ paraffin sulfonates and aryl sulfonates.

4. A detergency composition according to claim 3 wherein A is selected from the group consisting of $C_1$ to $C_{13}$ linear alkyl benzene sulfonates, and benzene sulfonates.

5. A detergency composition according to claim 4 wherein the wax component is a hydrocarbon wax which is selected from the group consisting of paraffin waxes with a melting point range of from about 120° F. (50° C.) to about 175° F. (80° C.) and a penetration of from about 10 to about 20 at 77° F. (25° C.), microcrystalline waxes with a melting point of from about 150° F. (66° C.) to about 220° F. (104° C.) and a penetration of from about 1 to about 10 at 77° F. (25° C.), and mixtures thereof.

6. A detergency composition according to claim 5 wherein the ratio of alkyl amine to anionic surfactant ranges from about 1:10 to about 10:1.

7. A detergency composition according to claim 3 wherein said alkyl amine-anionic surfactant ion pair complex is selected from the group consisting of ditallow amine (hydrogenated or unhydrogenated) complexed with a linear $C_1$–$C_{20}$ alkylbenzene sulfonate (LAS),
ditallow methyl amine (hydrogenated or unhydrogenated) complexed with a $C_1$–$C_{20}$ LAS,
dipalmityl amine complexed with a $C_1$–$C_{20}$ LAS,
dipalmityl methyl amine complexed with a $C_1$–$C_{20}$ LAS,
distearyl amine complexed with a $C_1$–$C_{20}$ LAS,
distearyl methyl amine complexed with a $C_1$–$C_{20}$ LAS,
diarachidyl amine complexed with a $C_1$–$C_{20}$ LAS,
diarachidyl methyl amine complexed with a $C_1$–$C_{20}$ LAS,
palmityl stearyl amine complexed with a $C_1$–$C_{20}$ LAS,
palmityl stearyl methyl amine complexed with a $C_1$–$C_{20}$ LAS,
palmityl arachidyl amine complexed with a $C_1$–$C_{20}$ LAS,
palmityl arachidyl methyl amine complexed with a $C_1$–$C_{20}$ LAS,
stearyl arachidyl amine complexed with a $C_1$–$C_{20}$ LAS,
stearyl arachidyl methyl amine complexed with a $C_1$–$C_{20}$ LAS,
ditallow amine (hydrogenated or unhydrogenated) complexed with a $C_1$–$C_{20}$ AS,
ditallow methyl amine (hydrogenated or unhydrogenated) complexed with a $C_1$–$C_{20}$ alkyl sulfonate (AS),
dipalmityl amine complexed with a $C_1$–$C_{20}$ AS,
dipalmityl methyl amine complexed with a $C_1$–$C_{20}$ AS,
distearyl amine complexed with a $C_1$–$C_{20}$ AS,
distearyl methyl amine complexed with a $C_1$–$C_{20}$ AS,
diarachidyl amine complexed with a $C_1$–$C_{20}$ AS,
diarachidyl methyl amine complexed with a $C_1$–$C_{20}$ AS,
palmityl stearyl amine complexed with a $C_1$–$C_{20}$ AS,
palmityl stearyl methyl amine complexed with a $C_1$–$C_{20}$ AS,
palmityl arachidyl amine complexed with a $C_1$–$C_{20}$ AS,
palmityl arachidyl methyl amine complexed with a $C_1$–$C_{20}$ AS,
stearyl arachidyl amine complexed with a $C_1$–$C_{20}$ AS,
stearyl arachidyl methyl amine complexed with a $C_1$–$C_{20}$ AS,
ditallow amine (hydrogenated or unhydrogenated) complexed with an aryl sulfonate,
ditallow methyl amine (hydrogenated or unhydrogenated) complexed with an aryl sulfonate,
dipalmityl amine complexed with an aryl sulfonate,
dipalmityl methyl amine complexed with an aryl sulfonate,
distearyl amine complexed with an aryl sulfonate,
distearyl methyl amine complexed with an aryl sulfonate,
diarachidyl amine complexed with an aryl sulfonate,
diarachidyl methyl amine complexed with an aryl sulfonate,
palmityl stearyl amine complexed with an aryl sulfonate,
palmityl stearyl methyl amine complexed with an aryl sulfonate,
palmityl arachidyl amine complexed with an aryl sulfonate, and
palmityl arachidyl methyl amine complexed with an aryl sulfonate,
stearyl arachidyl amine complexed with an aryl sulfonate, and
stearyl arachidyl methyl amine complexed with an aryl sulfonate,
and mixtures of these ion-pair complexes.

8. A detergency composition according to claim 6 wherein the amine portion is hydrogenated ditallow amine and wherein said composite has an average particle diameter of from about 10 to about 150 microns.

9. A detergency composition according to claim 8 wherein the builder component comprises from about 5.0% to about 30% of the total composition and is selected from the group consisting of polyacetates, inorganic phosphates, carbonates, silicates, water-insoluble alumino silicates, polyphosphonates, polycarboxylates, polymeric carboxylates, and acids, alkali metal salts, ammonium salts, and substituted ammonium salts thereof, and mixtures thereof.

10. A detergency composition according to claim 9 wherein the builder component is selected from the group consisting of polyacetates, nitriloacetic acid polycarboxylates, inorganic phosphates, alkenyl succinates, their salts, and mixtures thereof.

11. A detergency composition according to claim 9, wherein said builder component includes a succinate builder, or a salt or acid thereof.

12. A detergency composition according to claim 10 additionally comprising from about 0.1% to about 10% of a chelating agent.

13. A detergency composition according to claim 12 wherein the chelating agent is an amino carboxylate and comprises from about 0.1% to about 3.0% of the composition.

14. A detergency composition according to claim 13 wherein said chelating agent is selected from the group consisting of ethylenediaminetetraacetates, N-hydroxyethylethylenediaminetriacetates, nitrilotriacetates, ethylenediamine tetrapropionates, triethylenetetraaminehexaacetates, diethylenetriaminepentaacetates, and ethanoldiglycines, alkali metal, ammonium or substituted ammonium salts thereof, and mixtures thereof.

15. A detergency composition according to claim 14 additionally comprising from about 0.05% to about 5.0% of a soil release agent.

16. A detergency composition according to claim 15 wherein said soil release agent is selected from the group consisting of hydroxy ether cellulosic polymers, copolymeric blocks of ethylene terephthalate polyethylene oxide, polypropylene oxide terephthalate, cationic guar gums, and mixtures thereof.

17. A detergency composition according to claim 16 which further comprises from about 0.01% to about 5.0% of a clay soil removal and anti-redeposition agent.

18. A detergency composition according to claim 17 wherein said clay soil removal and anti-redeposition agent is selected from the group consisting of ethoxylated monoamines, ethoxylated diamines, ethoxylated polyamines and mixtures thereof.

19. A detergency composition according to claim 18 wherein said clay soil removal and anti-redeposition agent is ethoxylated tetraethylenepentaimine.

20. A detergency composition according to claim 19 which further comprises from about 0.25% to about 2% of an enzyme.

21. A detergency composition according to claim 14 which is a granular detergent and which further comprises from about 4% to about 15% of a smectite clay softener.

22. A detergency composition according to claim 20 which is a liquid and which further comprises from about 0.1% to about 10.0% of a stabilizing agent.

23. A liquid detergent composition according to claim 22 wherein said stabilizing agent comprises from about 0.3% to about 1.5% of the total composition and is a quaternized montmorillonite clay or synthetic hectorite clay.

24. An article of manufacture adapted for use to provide fabric care benefits in an automatic laundry dryer comprising:
(a) a composite of: (i) from about 1% to about 99% of a fabric conditioning composition comprising one or more of an alkyl amine-anionic surfactant ion-pair complex of the formula:

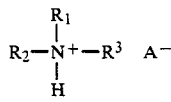

wherein $R_1$ and $R_2$ can independently be $C_{16}$ to $C_{20}$ alkyl or alkenyl, $R_3$ is H or $CH_3$, and A is an anionic surfactant selected from the group consisting of alkyl sulfonates, aryl sulfonates, alkylaryl sulfonates, alkyl sulfates, alkyl ethoxylated sulfates, dialkyl sulfosuccinates, ethoxylated alkyl sulfonates, alkyl oxybenzene sulfonates, acyl isethionates, acylalkyl taurates, olefin sulfonates and paraffin sulfonates, and mixtures of such ion-pair complexes; and (ii) from about 1% to about 99% of a nonsilicone wax; and
(b) a dispensing means which provides for release of an effective amount of said composition to fabrics in the dryer at automatic dryer operating temperatures.

25. An article according to claim 24 wherein said wax is a hydrocarbon wax and wherein said dispensing means comprises a flexible substrate in sheet configuration having the fabric conditioning composition releasably affixed thereto to provide a weight ratio of fabric conditioning composition to dry substrate ranging from about 10:1 to about 0.25:1.

26. An article according to claim 25 wherein A is selected from the group consisting of linear $C_1$ to $C_{20}$ alkyl sulfonates, linear $C_1$ to $C_{20}$ alkylaryl sulfonates, aryl sulfonates and $C_{12}$ to $C_{18}$ paraffin sulfonates.

27. An article according to claim 26 wherein the weight ratio of fabric conditioning composition:dry substrate ranges from 5:1 to about 1:1.

28. An article according to claim 27 wherein A is selected from the group consisting of $C_1$ to $C_{13}$ linear alkylbenzene sulfonates, benzene sulfonates and mixtures thereof.

29. A compact, through the wash laundry product comprising:
a laminate of two plies of which at least one ply comprises a strong, high stretch tissue which is deeply embossed to form one or a multiplicity of nonconnecting cups surrounded by rims;
the tissue in each cup having been stretched 15% to 100% by said deep embossing;
said cups containing from about 1% to about 100% of a water-insoluble composite having an average diameter of from about 10 to about 300 microns, comprising (i) from about 1 to about 99% of an alkyl amine-anionic surfactant ion-pair complex having the formula:

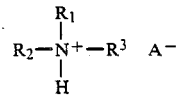

wherein $R_1$ and $R_2$ can independently be $C_{16}$ alkyl or alkenyl, $R_3$ is H or $CH_3$, and A is an anionic surfactant selected from the group consisting of alkyl sulfonates, aryl sulfonates, alkylaryl sulfonates, alkyl sulfates, alkyl ethoxylated sulfates, dialkyl sulfosuccinates, ethoxylated alkyl sulfonates, alkyl oxybenzene sulfonates, acyl isethionates, acylalkyl taurates, olefin sulfonates and paraffin sulfonates, and mixtures of such ion-pair complexes; and (ii) from about 99% to about 1% of a nonsilicone wax; and
the other of said two plies covering the deeply embossed ply forming patterned cells which contain the powder, said plies being sealed on said rims to provide said compact, through the wash laundry product;
said high stretch embossed tissue originally having a dry CD stretch of from about 9% to about 25% and a dry MD stretch of from about 30% to about 60%, a wet cross-directional tensile strength of from about 78.7 to about 315 g/cm (200-800 g/in), said one ply selected to withstand the stretching and said two plies selected to survive automatic washing and drying cycles without significant tearing; said tissue having sufficient porosity to permit the laundry actives to flow through the tissue.

30. The laundry product of claim 29 wherein said cups also contain a laundry active, said active being selected from powdered detergents, builders, brighteners, softeners, enzymes, bleach solids, fillers, and mixtures thereof.

31. The laundry product of claim 29 wherein said cups also contain a smectite clay softening agent.

32. A detergency composition comprising:
A. from about 1% to about 98% of a water-soluble detergent surfactant selected from the group consisting of cationic surfactants, nonionic surfactants, zwitterionic surfactants, amphoteric surfactants and anionic surfactants and mixtures thereof;
B. from about 0.1% to about 20% of a water-insoluble composite having an average diameter of from about 10 to about 300 microns, comprising (i) from about 1 to about 99% of an alkyl amine-anionic surfactant ion-pair complex having the formula:

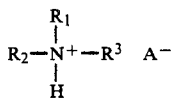

wherein $R_1$ and $R_2$ can independently be $C_{16}$ to $C_{20}$ alkyl or alkenyl, $R_3$ is H or $CH_3$, and A is an anionic surfactant selected from the group consisting of alkyl sulfonates, aryl sulfonates, alkylaryl sulfonates, alkyl sulfates, dialkyl sulfosuccinates, alkyl oxybenzene sulfonates, acyl isethionates, acylalkyl taurates, olefin sulfonates, alkyl ethoxylated sulfates and paraffin sulfonates, and mixtures of such ion-pair complexes; and (ii) from about 99% to about 1% of a nonsilicone wax; and
C. from about 0.25% to about 2% of an enzyme.

33. A detergency composition agent according to claim 32 wherein said ion-pair/wax composites have an average diameter of from about 10 to about 250 microns.

34. A detergency composition according to claim 33 wherein A is selected from the group consisting of linear $C_1$-$C_{20}$ alkyl sulfonates, linear $C_1$ to $C_{20}$ alkylaryl sulfonates, $C_{12}$ to $C_{18}$ paraffin sulfonates and aryl sulfonates.

35. A detergency composition according to claim 34 wherein A is selected from the group consisting of $C_1$ to $C_{13}$ linear alkyl benzene sulfonates, and benzene sulfonates.

36. A detergency composition according to claim 35 wherein the wax component is a hydrocarbon wax which is selected from the group consisting of paraffin waxes with a melting point range of from about 120° F. (50° C.) to about 175° F. (80° C.) and a penetration of from about 10 to about 20 at 77° F. (25° C.), microcrystalline waxes with a melting point of from about 150° F. (66° C.) to about 220° F. (104° C.) and a penetration of from about 1 to about 10 at 77° F. (25° C.), and mixtures thereof.

37. A detergency composition according to claim 36 wherein the ratio of alkyl amine to anionic surfactant ranges from about 1:10 to about 10:1.

38. A detergency composition according to claim 34 wherein said alkyl amine-anionic surfactant ion pair complex is selected from the group consisting of
ditallow amine (hydrogenated or unhydrogenated) complexed with a linear $C_1$-$C_{20}$ alkylbenzene sulfonate (LAS),
ditallow methyl amine (hydrogenated or unhydrogenated) complexed with a $C_1$-$C_{20}$ LAS,
dipalmityl amine complexed with a $C_1$-$C_{20}$ LAS,
dipalmityl methyl amine complexed with a $C_1$-$C_{20}$ LAS,
distearyl amine complexed with a $C_1$-$C_{20}$ LAS,
distearyl methyl amine complexed with a $C_1$-$C_{20}$ LAS,
diarachidyl amine complexed with a $C_1$-$C_{20}$ LAS,
diarachidyl methyl amine complexed with a $C_1$-$C_{20}$ LAS,
palmityl stearyl amine complexed with a $C_1$-$C_{20}$ LAS,
palmityl stearyl methyl amine complexed with a $C_1$-$C_{20}$ LAS,
palmityl arachidyl amine complexed with a $C_1$-$C_{20}$ LAS,
palmityl arachidyl methyl amine complexed with a $C_1$-$C_{20}$ LAS,
stearyl arachidyl amine complexed with a $C_1$-$C_{20}$ LAS,
stearyl arachidyl methyl amine complexed with a $C_1$-$C_{20}$ LAS,
ditallow amine (hydrogenated or unhydrogenated) complexed with a $C_1$-$C_{20}$ AS,
ditallow methyl amine (hydrogenated or unhydrogenated) complexed with a $C_1$-$C_{20}$ alkyl sulfonate (AS),
dipalmityl amine complexed with a $C_1$-$C_{20}$ AS,
dipalmityl methyl amine complexed with a $C_1$-$C_{20}$ AS,
distearyl amine complexed with a $C_1$-$C_{20}$ AS,
distearyl methyl amine complexed with a $C_1$-$C_{20}$ AS,
diarachidyl amine complexed with a $C_1$-$C_{20}$ AS,
diarachidyl methyl amine complexed with a $C_1$-$C_{20}$ AS,
palmityl stearyl amine complexed with a $C_1$-$C_{20}$ AS,
palmityl stearyl methyl amine complexed with a $C_1$-$C_{20}$ AS,
palmityl arachidyl amine complexed with a $C_1$-$C_{20}$ AS,
palmityl arachidyl methyl amine complexed with a $C_1$-$C_{20}$ AS,
stearyl arachidyl amine complexed with a $C_1$-$C_{20}$ AS,
stearyl arachidyl methyl amine complexed with a $C_1$-$C_{20}$ AS,
ditallow amine (hydrogenated or unhydrogenated) complexed with an aryl sulfonate,
ditallow methyl amine (hydrogenated or unhydrogenated) complexed with an aryl sulfonate,
dipalmityl amine complexed with an aryl sulfonate,
dipalmityl methyl amine complexed with an aryl sulfonate,
distearyl amine complexed with an aryl sulfonate,
distearyl methyl amine complexed with an aryl sulfonate,
diarachidyl amine complexed with an aryl sulfonate,
diarachidyl methyl amine complexed with an aryl sulfonate,
palmityl stearyl amine complexed with an aryl sulfonate,
palmityl stearyl methyl amine complexed with an aryl sulfonate,
palmityl arachidyl amine complexed with an aryl sulfonate, and
palmityl arachidyl methyl amine complexed with an aryl sulfonate,
stearyl arachidyl amine complexed with an aryl sulfonate, and
stearyl arachidyl methyl amine complexed with an aryl sulfonate,
and mixtures of these ion-pair complexes.

39. A detergency composition according to claim 36 wherein the amine portion is ditallow or distearyl amine and wherein said composite has an average particle diameter of from about 10 to about 150 microns.

40. A detergency composition according to claim 39 which is a fabric detergent additionally comprising from about 5% to about 50% of a detergency builder.

* * * * *